United States Patent
Wang et al.

(10) Patent No.: US 10,448,850 B2
(45) Date of Patent: Oct. 22, 2019

(54) PHOTOACOUSTIC FLOWMETRY SYSTEMS AND METHODS

(71) Applicant: Washington University, St. Louis, MO (US)

(72) Inventors: Lihong Wang, St. Louis, MO (US); Yong Zhou, St. Louis, MO (US)

(73) Assignee: Washington University, St. Louis, MO (US)

(*) Notice: Subject to any disclaimer, the term of this patent is extended or adjusted under 35 U.S.C. 154(b) by 214 days.

(21) Appl. No.: 15/289,319

(22) Filed: Oct. 10, 2016

(65) Prior Publication Data

US 2017/0105636 A1 Apr. 20, 2017

Related U.S. Application Data

(60) Provisional application No. 62/242,516, filed on Oct. 16, 2015.

(51) Int. Cl.
| | |
|---|---|
| *A61B 5/0275* | (2006.01) |
| *A61B 5/00* | (2006.01) |
| *A61B 5/0295* | (2006.01) |
| *A61B 5/022* | (2006.01) |

(52) U.S. Cl.
CPC .......... *A61B 5/0275* (2013.01); *A61B 5/0095* (2013.01); *A61B 5/0295* (2013.01); *A61B 5/7278* (2013.01); *A61B 5/02233* (2013.01)

(58) Field of Classification Search
CPC .... A61B 8/00; A61B 8/06; A61B 5/02; A61K 49/22
USPC .................................................. 600/438, 458
See application file for complete search history.

(56) References Cited

U.S. PATENT DOCUMENTS

| | | | |
|---|---|---|---|
| 2005/0049507 A1* | 3/2005 | Clark ................. | A61B 5/02007 600/458 |
| 2012/0089020 A1* | 4/2012 | Nitta .................. | A61B 5/02007 600/438 |
| 2014/0142404 A1 | 5/2014 | Wang et al. | |
| 2016/0249812 A1 | 9/2016 | Wang et al. | |

OTHER PUBLICATIONS

Beard, P. "Biomedical photoacoustic imaging," Interface Focus, 1(4): 602-631 (2011).

(Continued)

*Primary Examiner* — Jon Eric C Morales
(74) *Attorney, Agent, or Firm* — Armstrong Teasdale LLP

(57) ABSTRACT

Methods for measuring blood flow speed within blood vessels using a PA imaging system are disclosed. The methods include position a field of view of a PA imaging system along a section of a blood vessel, introducing a PA discontinuity into the blood flow within the blood vessel upstream of the FOV of the PA system, monitoring the movement of the PA discontinuity during movement through the FOV of the PA imaging device, and calculate the blood flow speed using at least two measured positions and corresponding times of the PA discontinuity within the FOV of the PA imaging system. PA discontinuities may include blood surges formed by compressing and releasing the blood vessel and/or boluses of a fluid with high PA contrast relative to the blood, such as saline solution.

20 Claims, 27 Drawing Sheets
(24 of 27 Drawing Sheet(s) Filed in Color)

(56) References Cited

OTHER PUBLICATIONS

Brunker et al. "Pulsed photoacoustic Doppler flowmetry using time-domain cross-correlation: Accuracy, resolution and scalability," Journal of the Acoustical Society of America, 132(3): 1780-1791 (2012).
Chen et al. "Photoacoustic correlation spectroscopy and its application to low-speed flow measurement," Optics Letters, 35(8): 1200-1202 (2010).
Fang et al. "Photoacoustic doppler effect from flowing small light-absorbing particles," Physical Review Letters, 99 (18), 184501/1-4 (2007).
Guo et al. "On the speckle-free nature of photoacoustic tomography," Medical Physics, 36(9), 4084-4088 (2009).
Guo et al. "Dependence of photoacoustic speckles on boundary roughness," Journal of Biomedical Optics, 17(4), 046009/1-6 (2012).
Needles et al. "Development and Initial Application of a Fully Integrated Photoacoustic Micro-Ultrasound System," IEEE Transactions on Ultrasonics, Ferroelectrics, and Frequency Control, 60(5): 888-897 (2013).
Ning et al. "Simultaneous photoacoustic microscopy of microvascular anatomy, oxygen saturation, and blood flow," Optics Letters, 40(6): 910-913 (2015).
Ntziachristos, V. "Going deeper than microscopy: the optical imaging frontier in biology," Nature Methods, 7(8): 603-614 (2010).
Sheinfeld et al. "Photoacoustic thermal diffusion flowmetry," Biomedical Optics Express, 3(4): 800-813 (2012).
Song et al. "A combined method to quantify the retinal metabolic rate of oxygen using photoacoustic ophthalmoscopy and optical coherence tomography," Scientific Reports, 4(6525): 1-7 (2014).
Song et al. "Laser-scanning Doppler photoacoustic microscopy based on temporal correlation," Applied Physics Letters, 102(20): 203501/1-4 (2013).
Tang et al. "Noninvasive photoacoustic microscopy of methemoglobin in vivo," Journal of Biomedical Optics, 20(3): 036007/1-6 (2015).
Wang et al. "Ultrasonically Encoded Photoacoustic Flowgraphy in Biological Tissue," Physical Review Letters, 111(20): 204301/1-5 (2013).
Wang et al. "Biomedical Optics: Principles and Imaging," Wiley-Interscience, 2007, 11 pages (Table of Contents only).
Wang, L. "Multiscale photoacoustic microscopy and computed tomography," Nature Photonics, 3(9): 503-509 (2009).
Wang et al. "Photoacoustic Tomography: In Vivo Imaging from Organelles to Organs," Science, 335(6075): 1458-1462 (2012).
Xia et al. "Small-Animal Whole-Body Photoacoustic Tomography: A Review," IEEE Transactions on Biomedical Engineering, 61(5): 1380-1389 (2014).
Yang et al. "Simultaneous functional photoacoustic and ultrasonic endoscopy of internal organs in vivo," Nature Medicine, 18(8): 1297-1303 (2012).
Yao et al. "In vivo photoacoustic imaging of transverse blood flow by using Doppler broadening of bandwidth," Optics Letters, 35(9): 1419-1421 (2010).
Yeh et al. "Photoacoustic microscopy of blood pulse wave," Journal of Biomedical Optics, 17(7): 070504/1-3 (2012).
Zhou et al. "Calibration-free absolute quantification of particle concentration by statistical analyses of photoacoustic signals in vivo," Journal of Biomedical Optics, 19(3): 037001/1-8 (2014).
Zhou et al. "Calibration-free in vivo transverse blood flowmetry based on cross correlation of slow time profiles from photoacoustic microscopy," Optics Letters, 38(19): 3882-3885 (2013).
Zhou et al. "Handheld photoacoustic microscopy to detect melanoma depth in vivo," Optic Letters, 39(16): 4731-4734 (2014).
Zhou et al. "Handheld photoacoustic probe to detect both melanoma depth and volume at high speed in vivo," Journal of Biophotonics, 8(11-12): 961-967 (2015).
Zhou et al. "Photoacoustic microscopy of bilirubin in tissue phantoms," Journal Biomedical Optics, 17(12): 126019/14 (2012).
Zhou et al. "In vivo photoacoustic flowmetry at depths of the diffusive regime based on saline injection," Journal Biomedical Optics, 20(8): 087001/1-4 (2015).

\* cited by examiner

PHOTOACOUSTIC FLOWMETRY SYSTEMS AND METHODS

CROSS REFERENCE TO RELATED APPLICATIONS

This application claims the benefit of U.S. Provisional Patent Application Ser. No. 62/242,516 entitled "PHOTOACOUSTIC FLOWMETRY SYSTEMS AND METHODS" filed on Oct. 16, 2016, the entirety of which is hereby incorporated by reference.

STATEMENT REGARDING FEDERALLY SPONSORED RESEARCH & DEVELOPMENT

This invention was made with government support under grant DP1 EB016986 awarded by the National Institutes of Health. The government has certain rights to the invention.

FIELD OF THE INVENTION

The present invention relates to systems and methods of photoacoustic flowmetry systems and methods. In particular, the present invention relates to systems and methods of measuring blood flow rate using photoacoustic imaging in conjunction with detectable perturbations to the composition of blood following through a vessel induced by the release of a compressive cuff or a saline injection into the vessel.

BACKGROUND

Blood flow mapping provides important information for the diagnosis and treatment of many diseases, such as stroke and atherosclerosis. Doppler ultrasound (US) is a frequently used technique to measure blood flow in humans. However, because of the poor ultrasonic scattering contrast between blood and extravascular tissue, Doppler US cannot measure slow blood flow, which limits its use to evaluating blood flow in the major arteries and veins. Optical visualization methods, such as Doppler optical coherence tomography and laser speckle flowmetry, cannot measure blood flow in humans in the optical diffusive regime due to the limited penetration of ballistic photons in biological tissues.

With high blood detection contrast and deep penetrative reach, photoacoustic tomography (PAT) may provide a way to measure slow blood flow in the diffusive regime in humans. In PAT, short light pulses, usually from a laser, excite the target. Following absorption of the light, an initial temperature rise induces a pressure rise due to the photoacoustic (PA) effect. The pressure rise then propagates as a PA wave and is finally detected by an ultrasonic transducer. Each laser pulse yielded a one-dimensional depth-resolved PA image (A-line) by recording the time course of PA signals. Because blood absorbs visible light much more strongly than most other tissue components, PAT can detect blood with high contrast. In addition, by detecting ultrasonic signals, which have much lower scattering than optical signals in tissue, PAT can image deep tissues and structures with high spatial resolution. For example, PAT has detected blood vessels in vivo at depths as high as 3.5 cm.

Many PAT-based methods have been proposed to measure blood flow. Doppler PA detects absorption-based signals and calculates the flow velocity based on the frequency shift of these signals. However, Doppler PA is most effective for flows containing sparse particles, and the accuracy of Doppler PA is reduced when the detection axis is perpendicular to the flow direction. M-mode PA flowmetry quantifies the "slow-time" PA amplitudes, defined as a series of maximum PA amplitudes obtained from an A-line sequence, and estimates the flow speed by changes in the "slow-time" PA amplitudes induced by particle movement. M-mode PA flowmetry enabled measuring flow speeds perpendicular to the detection axis. Based on similar ideas, time-domain PA auto-correlation and frequency-domain PA Doppler bandwidth broadening have been used to measure blood flow in mice in vivo. To eliminate the measurement error resulting from the particle size, cross-correlation based PA flowmetry was also demonstrated in mice. For human imaging, however, because vessels are often more deeply embedded than they are in mice, PAT imaging of human vessels is characterized by significantly degraded spatial resolutions. As the detection voxel size increases, there is a corresponding decrease in the slow-time PA signal changes due to the flowing particles or red blood cells. When these changes in the slow-time PA signal changes due to the flowing particles are smaller than other PA signal changes induced by, for example, thermal noise, the extraction of flow information from the changes in the slow-time PA signals may be challenging.

Photoacoustic tomography (PAT) is a modality that provides imaging in either two dimensions (2D) or three dimensions (3D). Combining the advantages of optical excitation and acoustic detection, PAT can image rich optical absorption contrast in biological tissues at depths. To date, PAT has been widely used for both structural and functional biological imaging in many different fields, including hematology, oncology, dermatology, ophthalmology, and gastroenterology. Depending on the limiting factor for spatial resolution, PAT can be divided into optical-resolution PAT (OR-PAT) and acoustic-resolution PAT (AR-PAT). In OR-PAT, the optical focus is much tighter than the acoustic focus, and a high spatial resolution can be achieved. AR-PAT provides a lower spatial resolution, defined by the dimensions of acoustic focus achieved by the acoustic transducers. Nevertheless, because in biological tissue ultrasound suffers much less scattering than light, AR-PAT can achieve deep imaging with a depth-to-resolution ratio of more than 100. So far, with high resolution, OR-PAT has imaged a variety of important biological parameters in vivo, such as the oxygen saturation of hemoglobin ($sO_2$), pulse wave velocity, and the metabolic rate of oxygen ($MRO_2$). However, although AR-PAT has imaged $sO_2$ at depths corresponding to deep vessels, it still cannot provide in vivo blood flow information. In addition, in order to calculate $MRO_2$ in deep vessels with PAT, blood flow speed needs to be measured, which makes it even more important to quantify flow.

There are two fundamental reasons why it is difficult for AR-PAT to measure blood flow velocity. First, unlike ultrasound, PAT almost has no speckles. If the target has a smooth boundary with respect to the wavelengths of the PA waves, the boundary signals of the target will stand out, while the speckles inside the target are largely suppressed. Because blood vessels in biological tissues typically have smooth boundaries, it is challenging for PAT to extract blood flow information based on speckle fluctuations. Second, AR-PAT has a lower spatial resolution than OR-PAT and thus a larger detection voxel size. In typical OR-PAT imaging, the spatial resolution is comparable to the size of red blood cells (RBCs). Thus, when RBCs flow into and out of a detection voxel, the PA signal changes are observable. By monitoring how fast the signal changes, the flow velocity can be calculated. However, in AR-PAT, the large detection voxel contains many more RBCs than in OR-PAT. Because the number of RBCs inside the detection voxel can be assumed to follow a Poisson distribution, a larger mean number of RBCs leads to a smaller relative RBC number change and thus a smaller PA signal change. For example, if there are 10,000 RBCs in the detection voxel, the PA signal change due to the RBC number change would be only around 1%, so the AR-PAT system would need a signal-to-noise ratio (SNR) of more than 100 to measure the flow velocity.

Although challenging, different methods have been proposed to achieve blood flow measurement with AR-PAT, including PA Doppler (PAD) flowmetry and ultrasonically encoded PA flowgraphy (UE-PAF). Based on the PAD effect, different PAD shifts have been observed from particles moving with different flow speeds, and the Doppler theory allows the flow speeds to be calculated. However, to observe the PAD shift, the moving particles have to be very sparse. Thus, this method cannot measure the flow velocity of whole blood. But by using ultrasound to encode the PA signals, UE-PAF can achieve whole blood flow imaging in deep tissue. In UE-PAF, modulated ultrasound is focused into the blood vessel to create a heating source. Because PA signals are proportional to temperature, the PA signals from the heated area will increase. By monitoring the increased PA signals along the blood vessel, the flow speed in the blood vessel can be measured. However, this method's complexity has limited it to only phantoms, and so far, no in vivo data have been reported.

A need exists for a method of measuring slow blood flow within relatively deep vessels of human subjects using a PAT-based method.

SUMMARY

Provided herein is a method of measuring a velocity of a blood flow in a blood vessel using a photoacoustic imaging system. The method includes: positioning a field of view of the photoacoustic imaging system along a segment of the blood vessel; introducing a photoacoustic discontinuity into the blood flow at a position upstream of the field of view; measuring a change in position and a corresponding change in time of the photoacoustic discontinuity moving through the segment of the blood vessel using the photoacoustic imaging system; and calculating the velocity of the blood flow by dividing the change in position by the corresponding change in time.

Further provided herein is a method of measuring a velocity of a blood flow in a blood vessel using a photoacoustic imaging system. The method includes: positioning a field of view of the photoacoustic imaging system along a segment of the blood vessel; applying a compression to the blood vessel upstream of the field of view for a time sufficient to deplete the segment of the blood vessel of blood cells downstream of the compression and to form a blood surge upstream of the compression; releasing the compression from the blood vessel causing the blood surge to flow within the blood vessel to the field of view of the photoacoustic imaging system. The blood surge includes a dense bolus of blood cells bounded by a blood surge interface at a downstream end of the bolus. The method further includes measuring a change in position and a corresponding change in time of the blood surge interface moving through the field of view using the photoacoustic imaging system, and calculating the velocity of the blood flow by dividing the change in position by the corresponding change in time.

Additionally provided herein is a method of measuring a velocity of a blood flow in a blood vessel using a photoacoustic imaging system. The method includes: positioning a field of view of the photoacoustic imaging system along a segment of the blood vessel; injecting a bolus of a contrasting fluid into the blood vessel upstream of the field of view causing the bolus to flow within the blood vessel to the field of view of the photoacoustic imaging system. The bolus is bounded by a first fluid-blood-interface at an upstream end and by a second fluid-blood interface at a downstream end. The method further includes measuring a change in position and a corresponding change in time of the first fluid-blood-interface or the second fluid-blood-interface moving through the field of view using the photoacoustic imaging system; and calculating the velocity of the blood flow by dividing the change in position by the corresponding change in time.

BRIEF DESCRIPTION OF THE DRAWINGSCOLOR DRAWINGS

The patent or application file contains at least one drawing executed in color. Copies of this patent or patent application publication with color drawing(s) will be provided by the Office upon request and payment of the necessary fee.

The following figures illustrate various aspects of the disclosure.

Figure 5A:
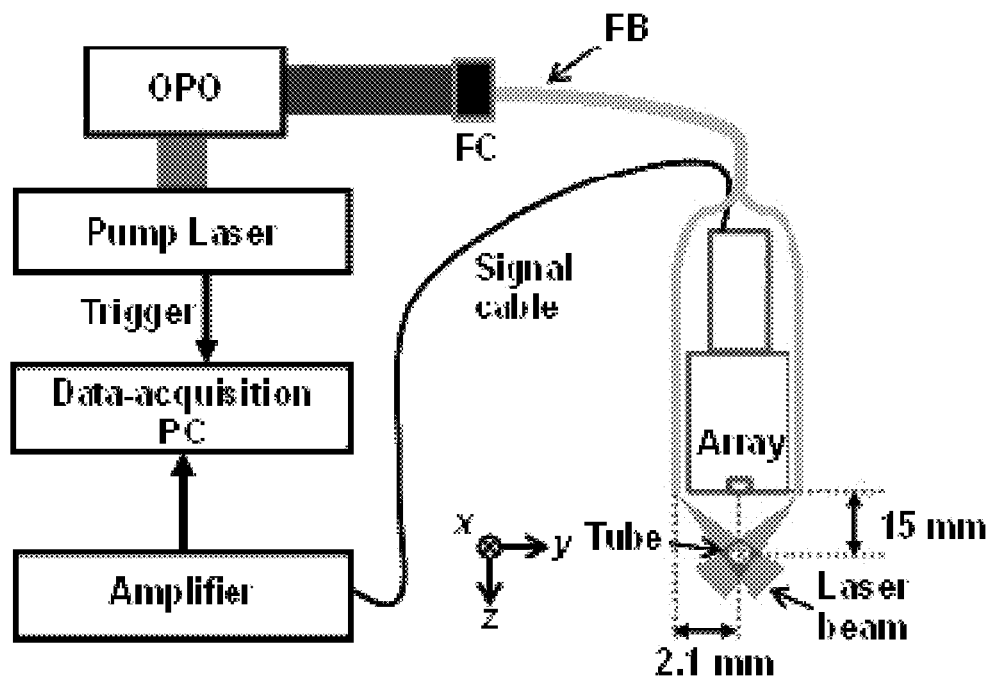

FIG. 5A is a schematic diagram of a photoacoustic tomography (PAT) system (FB, fiber bundle; FC, fiber coupler; OPO, optical parametric oscillator).

Figure 5B:
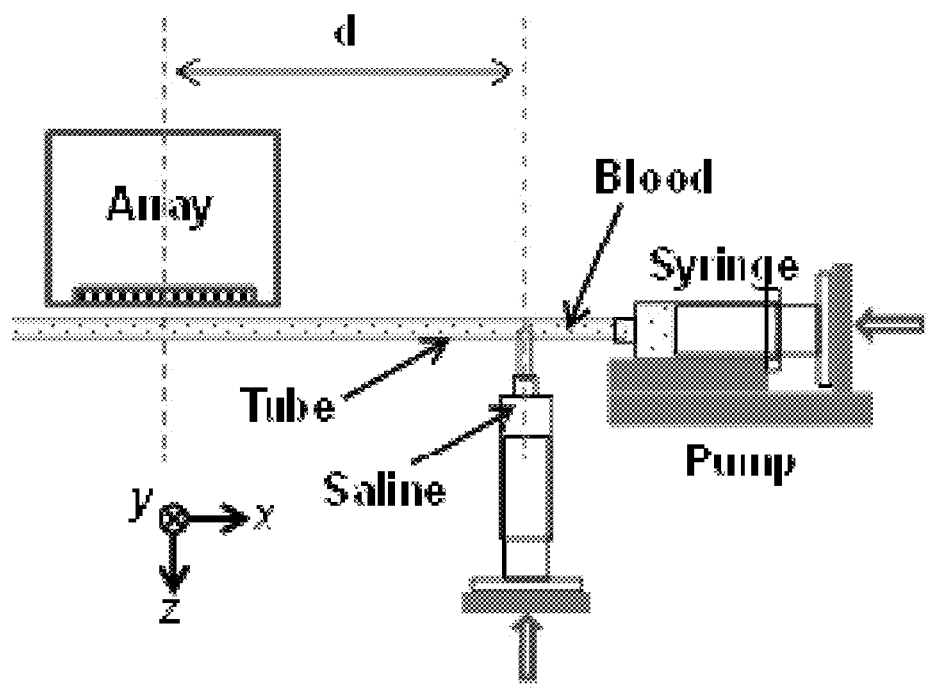

FIG. 5B is a schematic diagram of a saline injection apparatus and phantom blood vessel (d=15 cm).

Figure 6A:
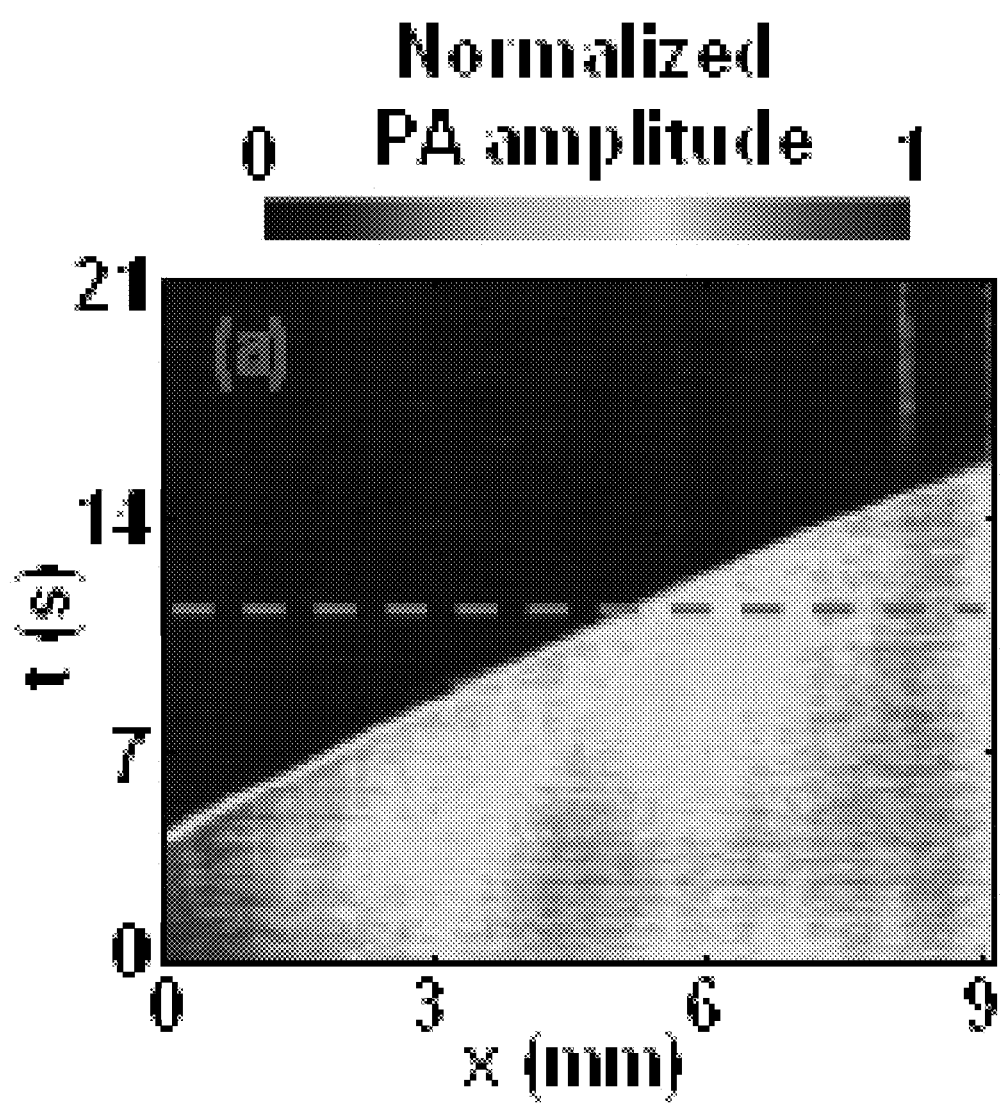

FIG. 6A is an image summarizing the time course of the photoacoustic (PA) amplitude measured from a phantom blood vessel after injection of a saline solution. Each horizontal line of pixels represents the PA amplitudes along a linear transect defined along the phantom blood vessel measured at a single sample time.

Figure 6B:
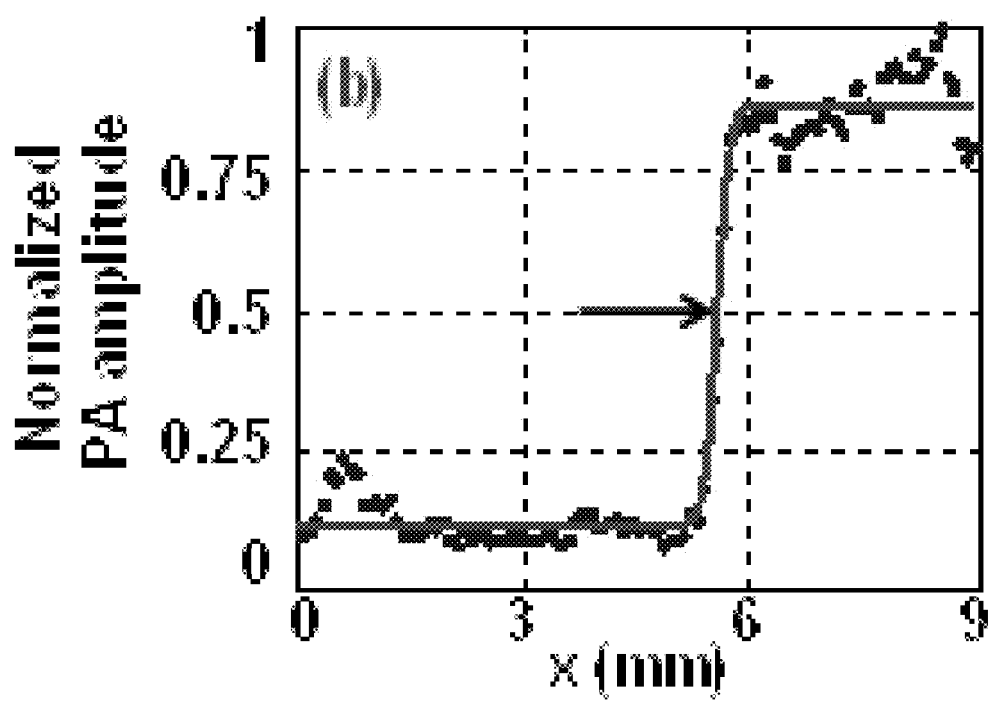

FIG. 6B is a graph of normalized PA amplitude measured along the phantom vessel at a single sample time after injection of the saline solution. Blue dots on the graph are the extracted one dimensional PA amplitudes along the dashed line transect in FIG. 6A, fitted with an error function fitting (red line). The mean value of the error function corresponding to the saline-blood-interface (SBI) is marked on the graph as a black arrow.

Figure 6C:
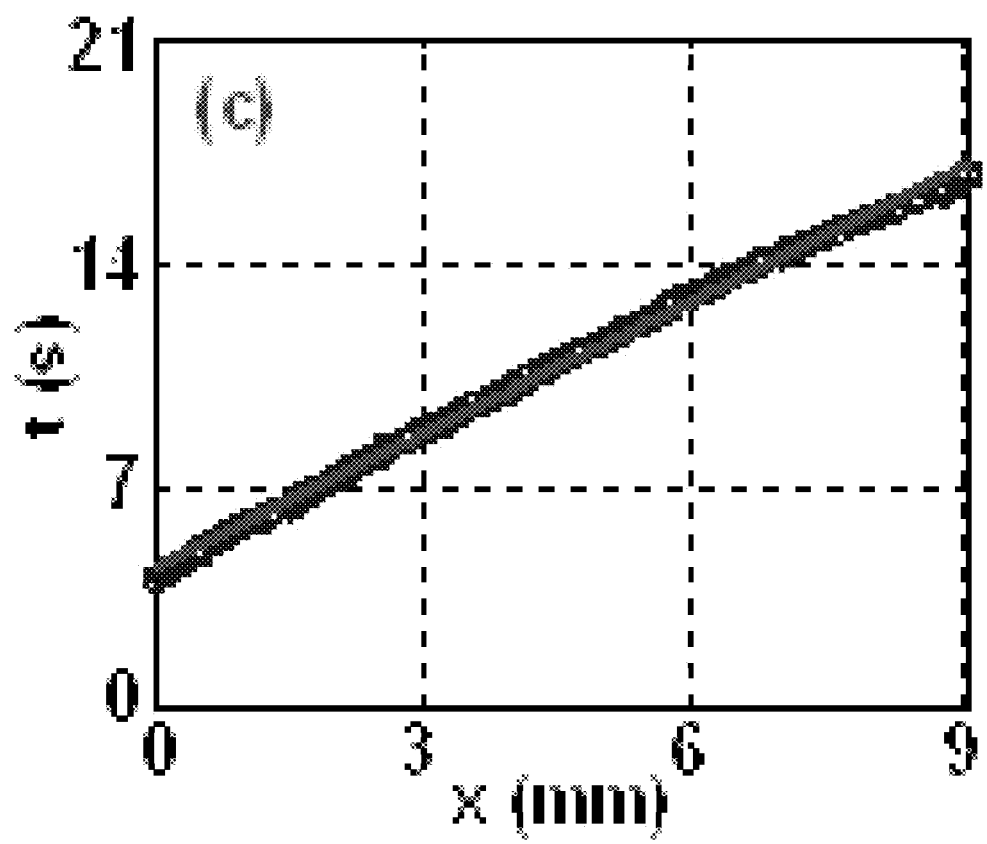

FIG. 6C is a graph summarizing the location of the saline-blood-interface (SBI) within the phantom blood vessel as the SBI passes down the phantom after an injection of saline solution. Each blue circle on the graph shown in FIG. 6C corresponds to the mean value of an error function fitted to the PA amplitude data at each corresponding time in a manner similar to that illustrated in FIG. 6B. The red line shown on the graph of FIG. 6C is a linear fit of the blue circles on this graph.

Figure 7A:
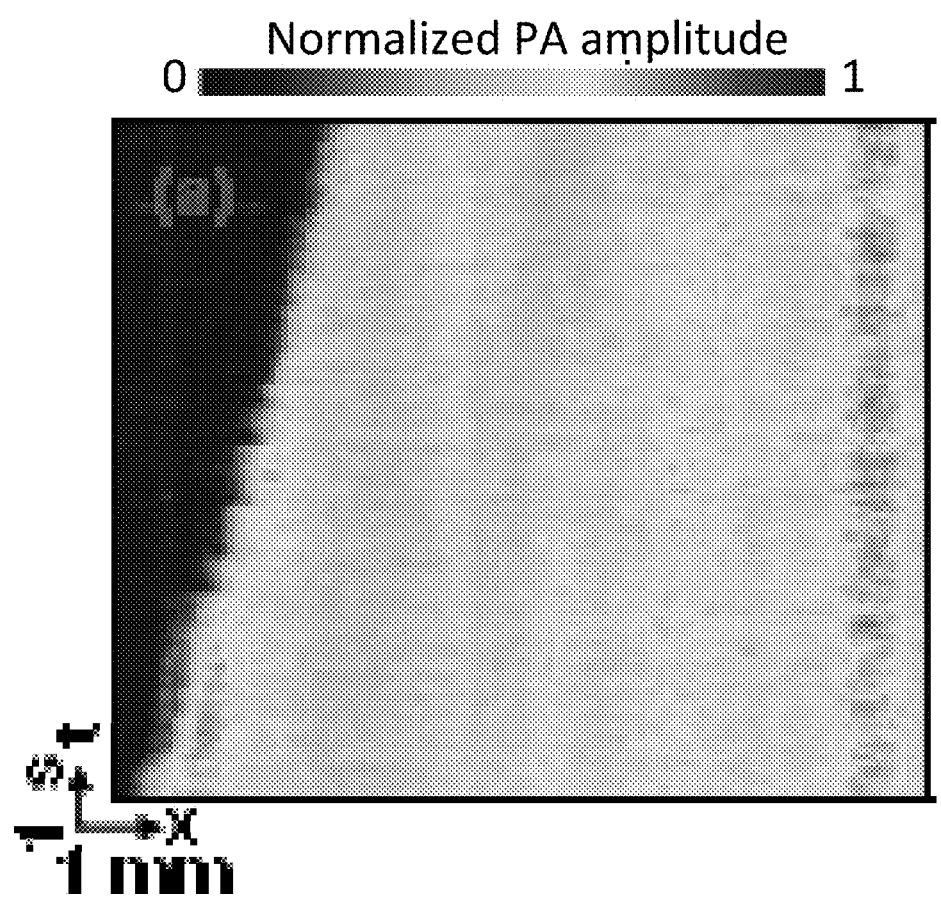

FIG. 7A is an image similar to the image of FIG. 6A summarizing the time course of the photoacoustic (PA) amplitude measured from a phantom blood vessel after injection of a saline solution, with a simulated flow rate of 0.2 mm/sec.

Figure 7B:
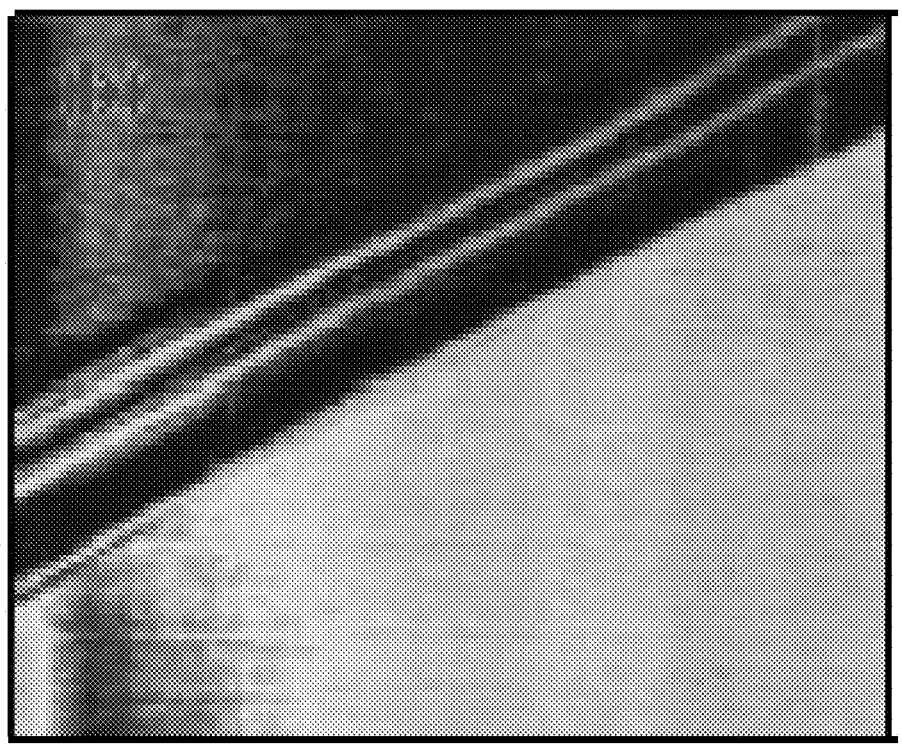

FIG. 7B is an image similar to the image of FIG. 6A summarizing the time course of the photoacoustic (PA) amplitude measured from a phantom blood vessel after injection of a saline solution, with a simulated flow rate of 1.3 mm/sec.

Figure 7C:
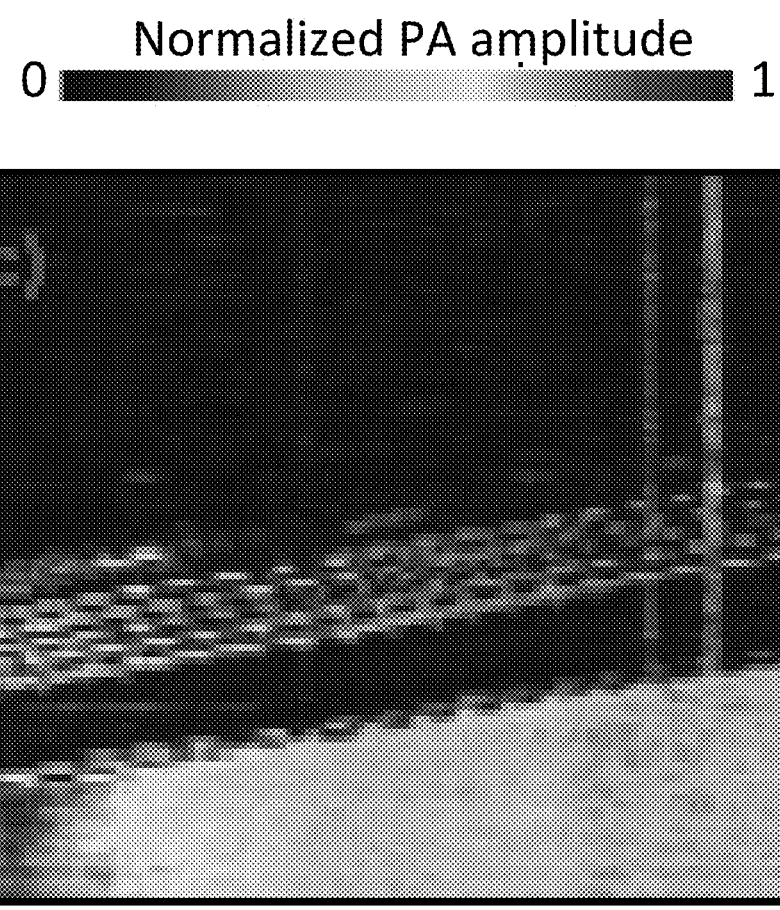

FIG. 7C is an image similar to the image of FIG. 6A summarizing the time course of the photoacoustic (PA) amplitude measured from a phantom blood vessel after injection of a saline solution, with a simulated flow rate of 4.5 mm/sec.

Figure 7D:
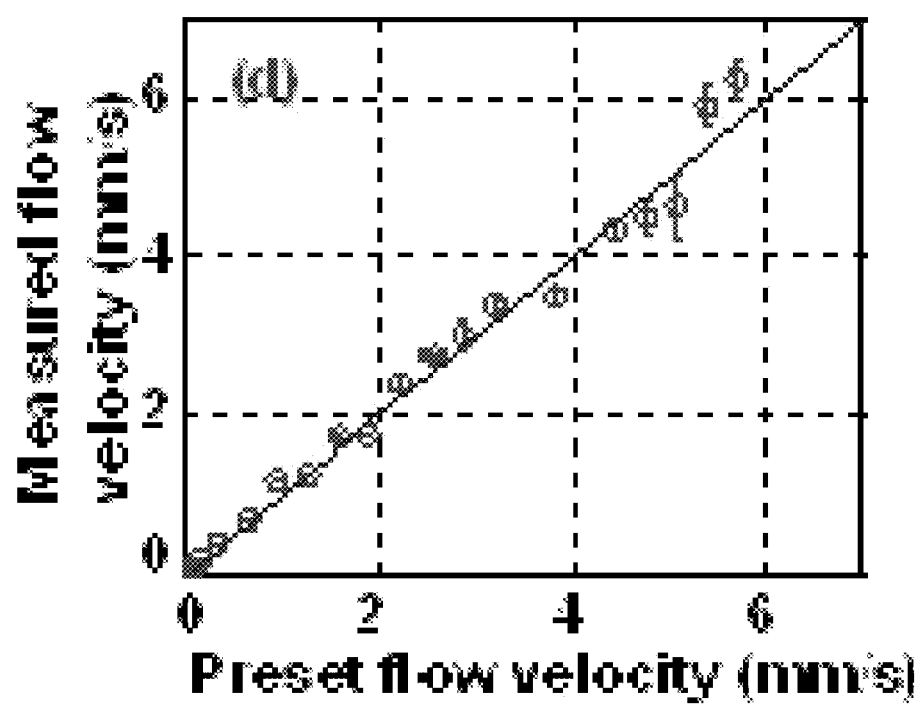

FIG. 7D is a graph summarizing the measured flow velocity as a function of the simulated flow velocity in a phantom blood vessel. Red circles represent the experimentally measured flow velocities and the blue line is a line representing prefect agreement between the experimentally measured flow velocities and simulated flow velocities.

Figure 8A:
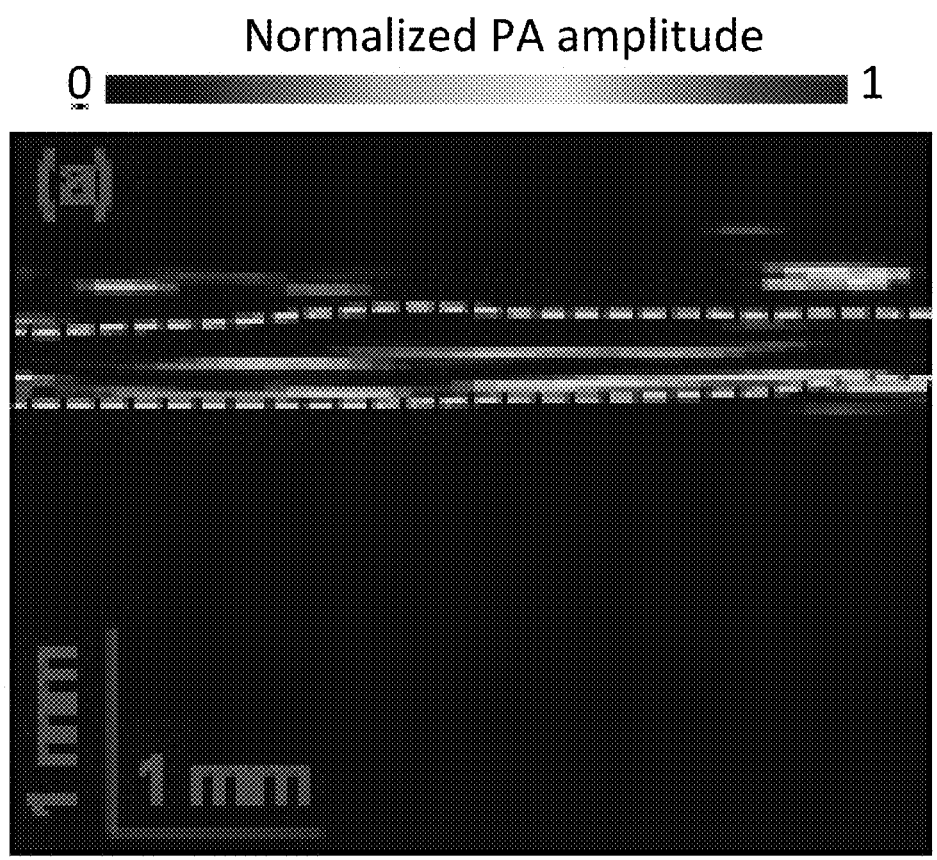

FIG. 8A is an image similar to the image of FIG. 6A summarizing the time course of the photoacoustic (PA) amplitude measured from a mouse tail vein prior to injection of a saline solution. Dashed lines indicate the vessel region.

Figure 8B:
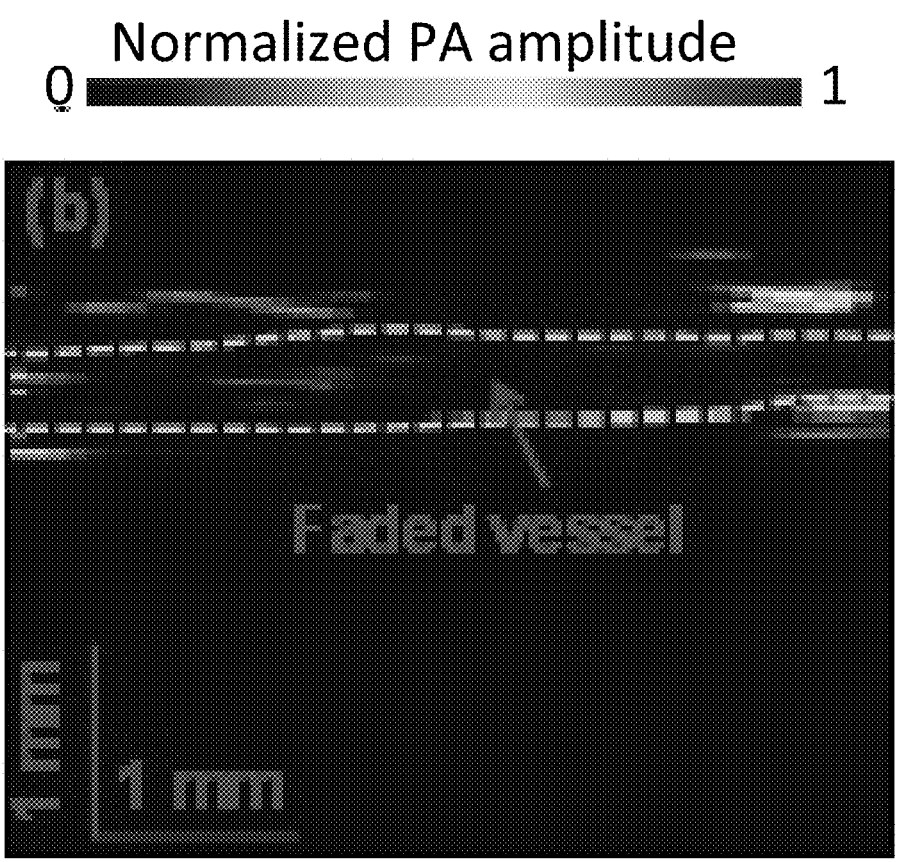

FIG. 8B is an image similar to the image of FIG. 6A summarizing the time course of the photoacoustic (PA) amplitude measured from a mouse tail vein after injection of a saline solution. Dashed lines indicate the vessel region.

Figure 8C:
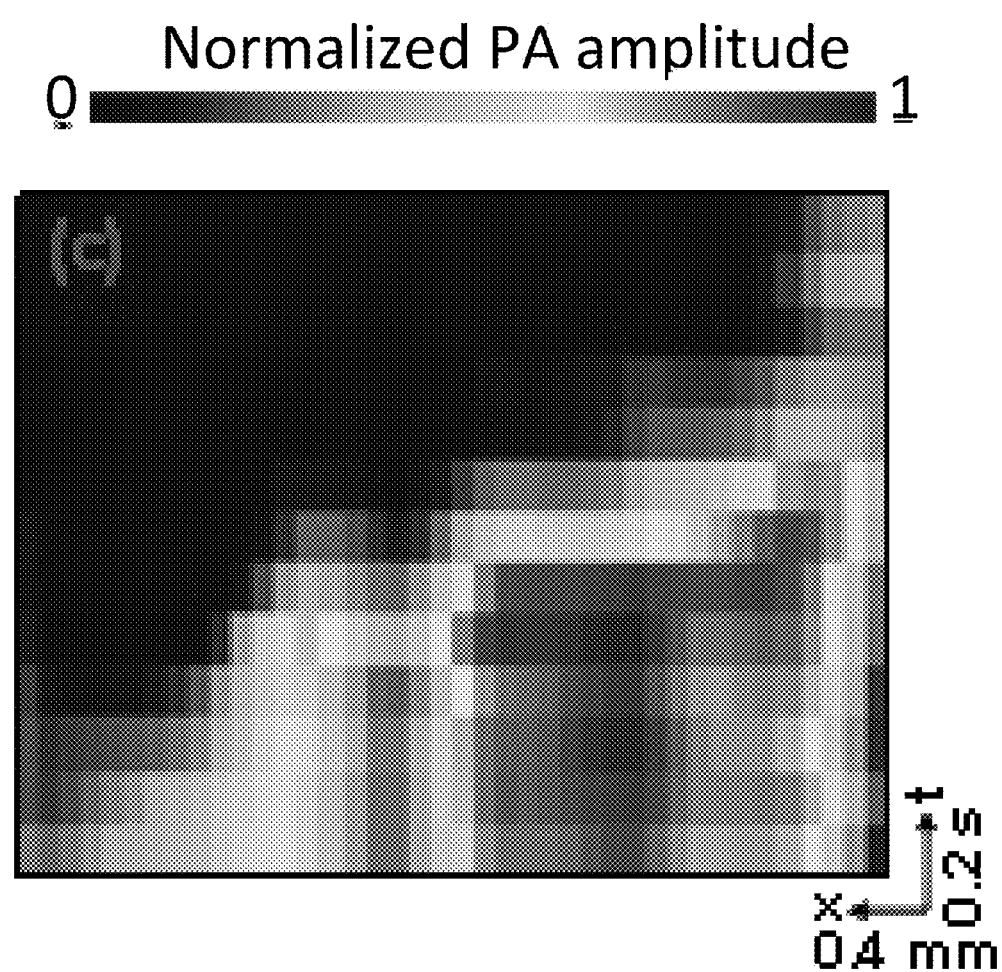

FIG. 8C is an image similar to the image of FIG. 6A summarizing the time course of the photoacoustic (PA) amplitude measured from a mouse tail vein as injected saline solution flushed through the mouse tail vein.

Figure 9:
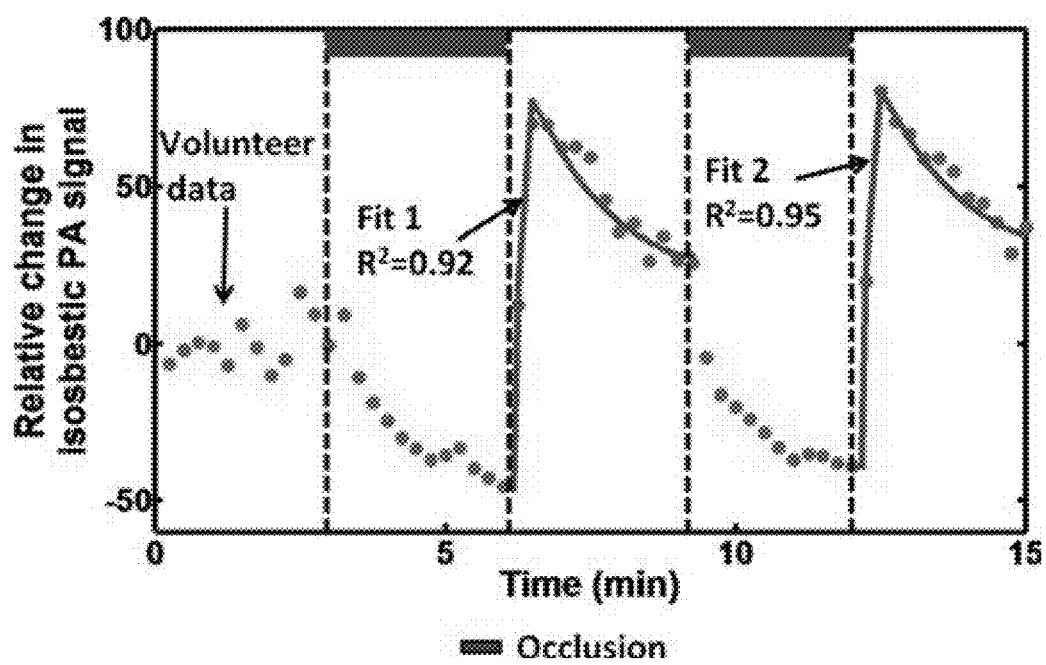

FIG. 9 is a graph summarizing the recovery of flow in a blood vessel after a series of occlusions measured from a subject diagnosed with peripheral arterial occlusive disease using a photoacoustic microscopy (PAM) system.

Figures 10A, 10B, 10C:
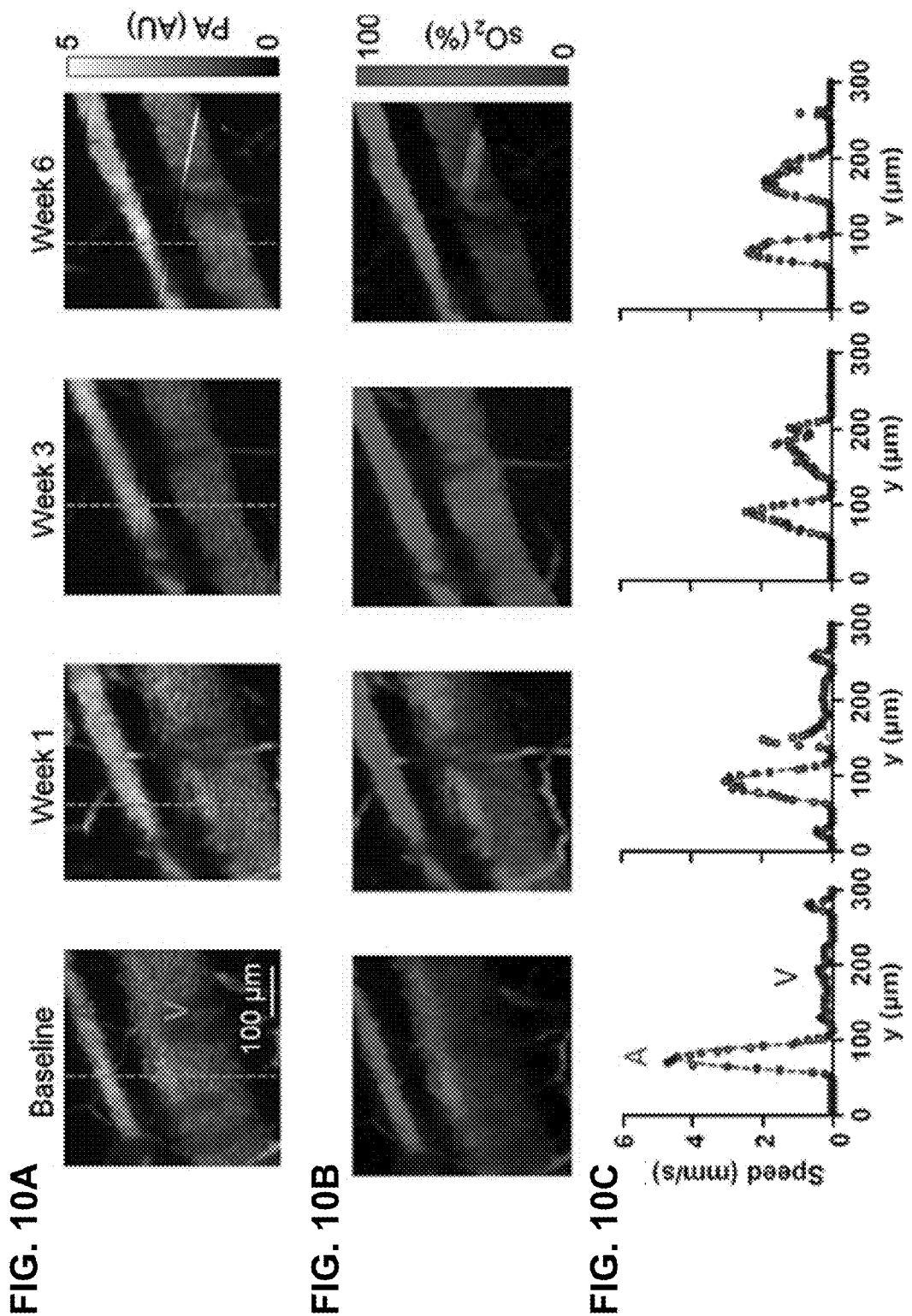

FIG. 10A is series of PA images summarizing PA amplitude (pixel intensity) as a function of position within the field of view of a photoacoustic microscopy (PAM) system. Each vertical pixel column represents the maximum PA amplitudes measured along all positions within the field of view of the PAM system at a single sample time; the horizontal axis corresponds to the sample times. Each image was obtained from a mouse tail vein for a diabetes mouse model at baseline (pre-diabetes) as well as 1, 3, and 6 weeks after induction of diabetes.

FIG. 10B is series of images summarizing oxygen saturation (% $sO_2$) measured using a PAM system and corresponding to the images of FIG. 10A.

FIG. 10C is series of graphs summarizing PAM-measured blood flow speed as a function of position within the field of view of the PAM system; each graph corresponds to the transects (represented as green dashed lines) in each of the images of FIG. 10A.

Figure 11:
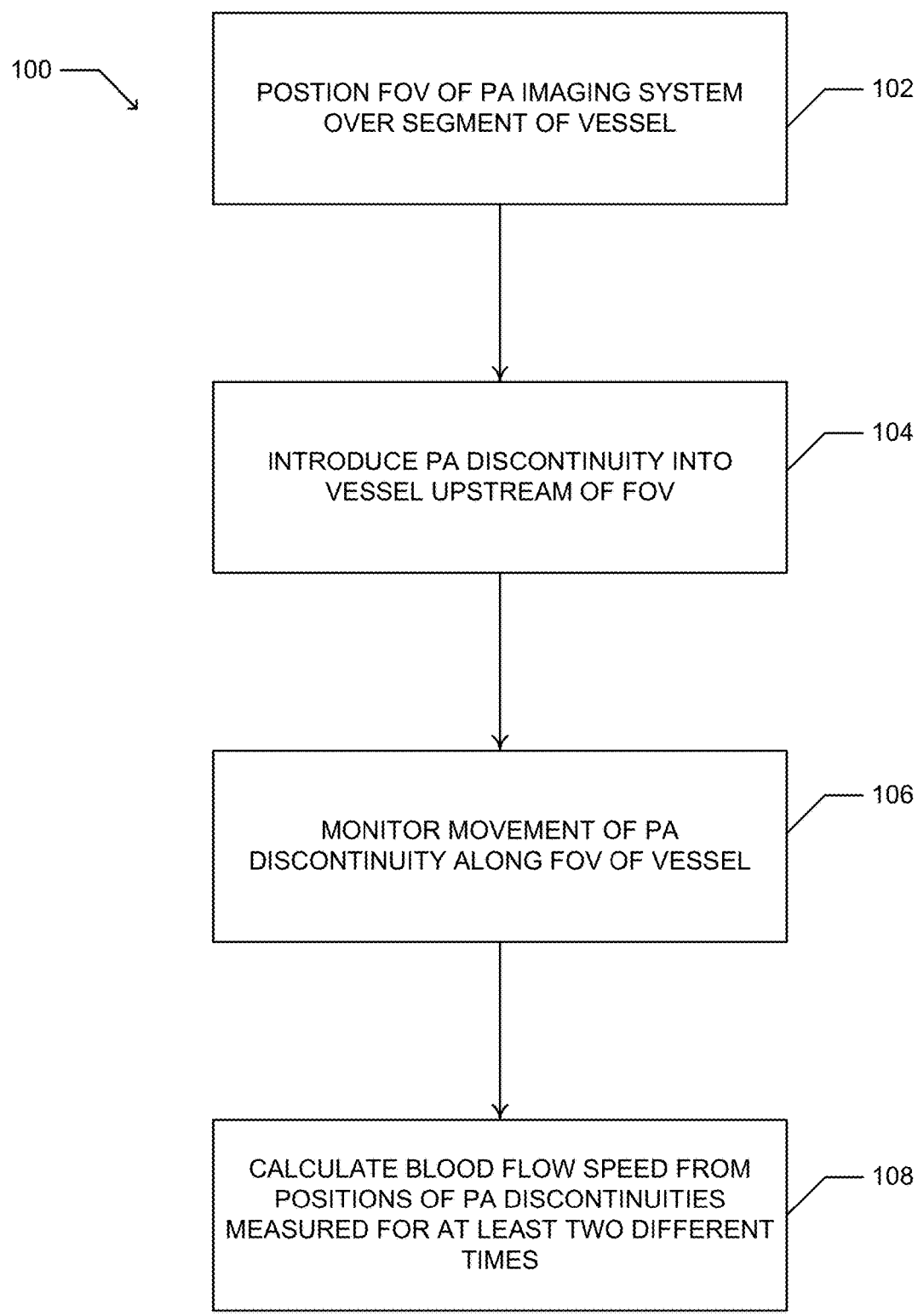

FIG. 11 is a flow chart summarizing the steps of a method of measuring blood flow speed in a blood vessel using a photoacoustic imaging device.

Figure 12:
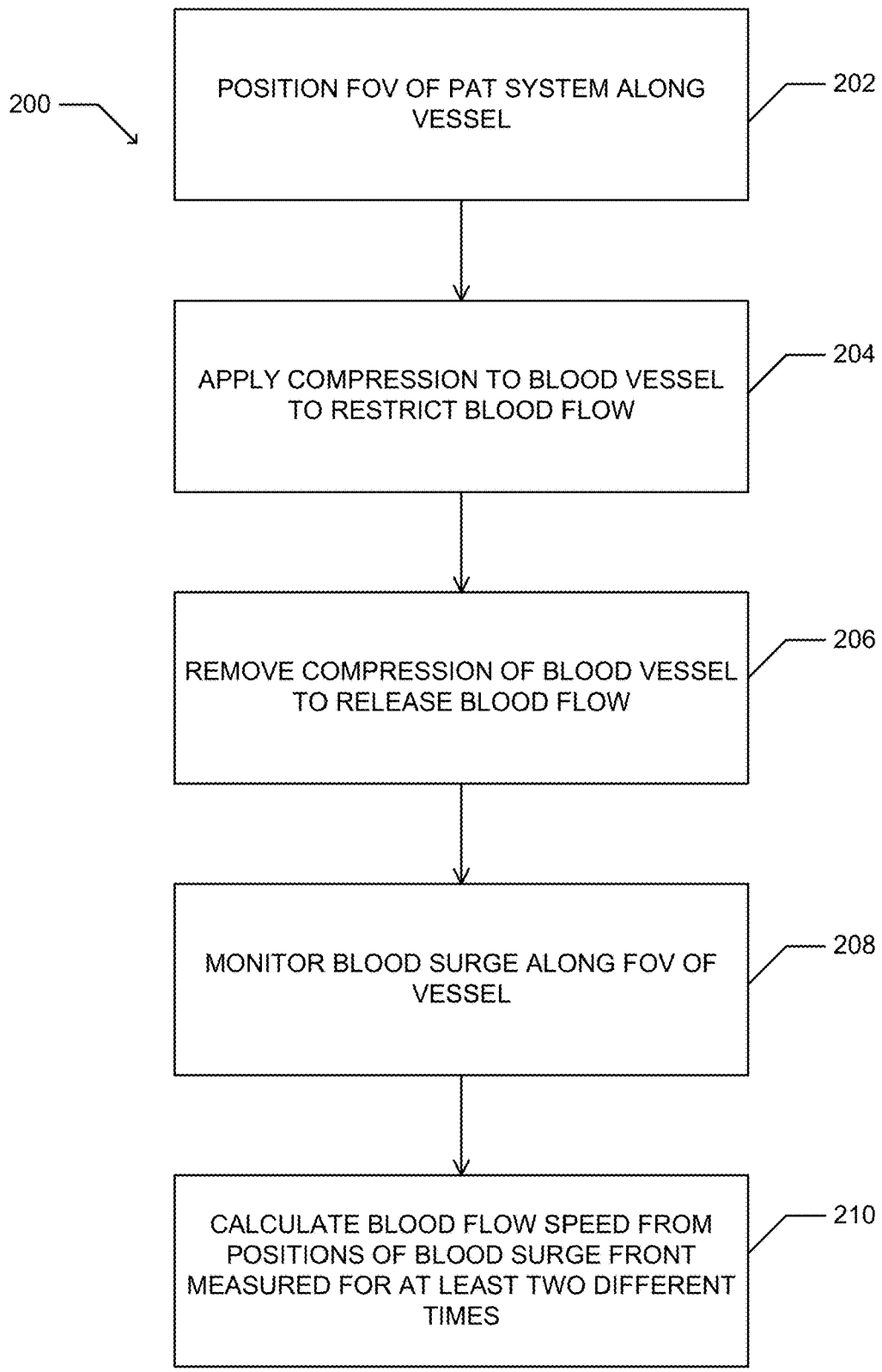

FIG. 12 is a flow chart summarizing the steps of a blood flow restriction-based method of measuring blood flow speed in a blood vessel using a photoacoustic imaging device.

Figure 13:
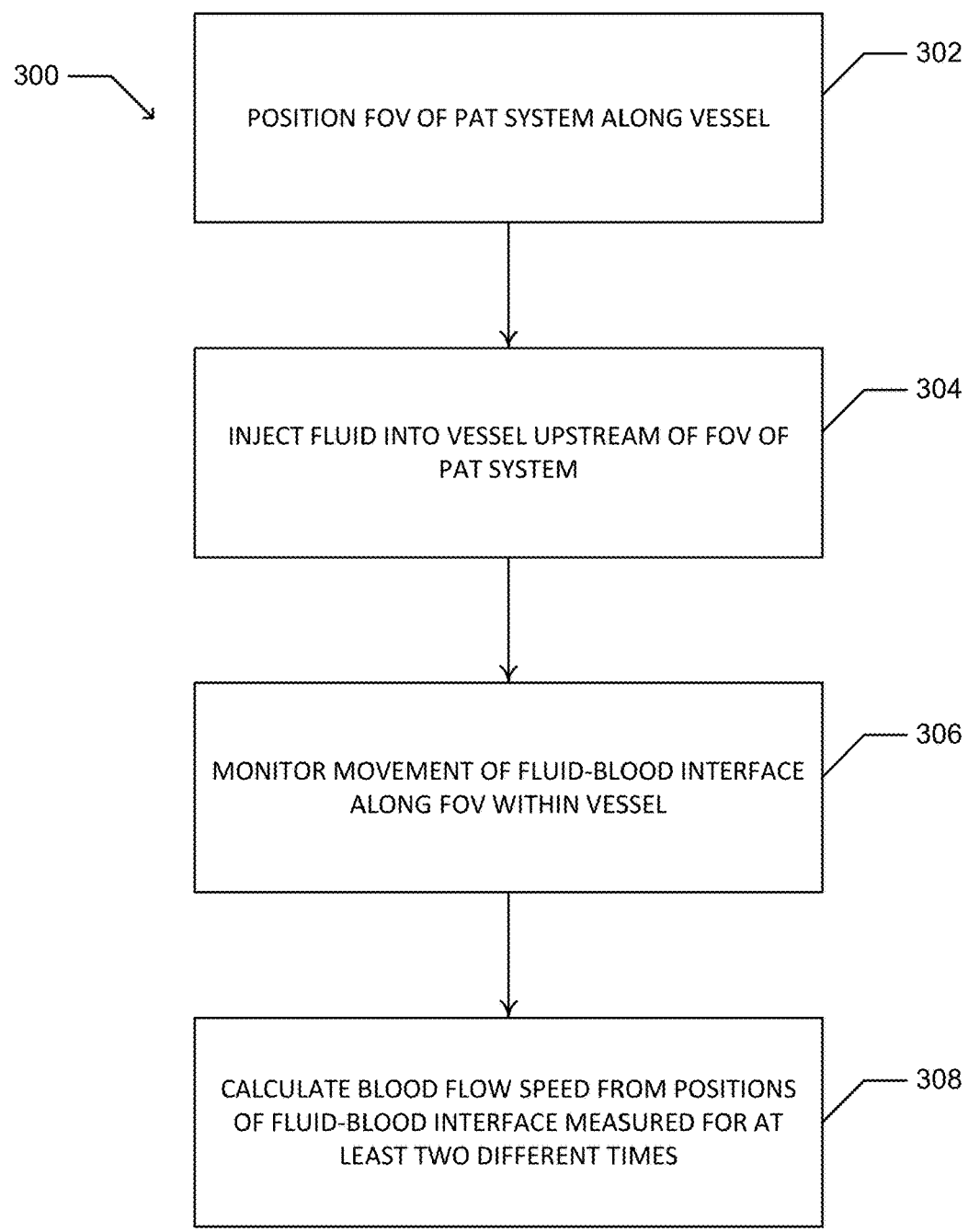

FIG. 13 is a flow chart summarizing the steps of a saline injection-based method of measuring blood flow speed in a blood vessel using a photoacoustic imaging device.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

Provided herein are methods of measuring the blood flow rate within a blood vessel in vivo using images of photoacoustic (PA) discontinuities within the blood flow obtained by a photoacoustic (PA) imaging system. FIG. 11 is a flow chart summarizing the steps of a method 100 in one aspect. The method 100 includes positioning a field of view (FOV) of the PA imaging system along a segment of the blood vessel at step 102. Any PA imaging system may be used to enable any of the methods described herein, including, but not limited to the method 100 described in FIG. 11. Non-limiting examples of suitable photoacoustic imaging systems include: acoustic resolution photoacoustic tomography (AR-PAT) systems; optical resolution photoacoustic tomography (OR-PAT) systems; handheld OR-PAT systems, and any other known photoacoustic imaging system. In one exemplary aspect, an acoustic resolution photoacoustic tomography (AR-PAT) system is used to obtain images of the PA discontinuities in the blood flow. Referring again to FIG. 11, the FOV may be aligned along the direction of blood flow within a segment of a blood vessel at step 102.

Referring again to FIG. 11, the method may further include introducing a PA signal discontinuity into the flow at a position upstream of the field of view (FOV) at step 104. A PA signal discontinuity, as used herein, refers to any region within the blood flow characterized by an abrupt spatial change in the PA signal produced by objects within the blood flow. The change in PA signal occurs over a relatively small distance, effectively labeling a portion of the blood flow that moves with the blood flow at the blood flow speed. The position of this labeled portion of the blood flow may be readily detected by the PA imaging system as described in detail herein below.

By way of non-limiting example, various blood cells within the blood flow including, but not limited to red blood cells and white blood cells, are capable of producing relatively strong PA signals depending on the wavelength, pulse duration, fluence, and any other relevant factor characterizing the laser pulses produced by the PA imaging system. In various aspects, the PA discontinuity may be any abrupt change in concentration of blood cells within the blood flow. Non-limiting examples of PA discontinuities suitable for use in the method 100 and all other methods described herein include a blood surge and a bolus of a contrasting fluid, both described in detail herein below.

Referring again to FIG. 11, the method 100 further includes monitoring the movement of the PA discontinuity as it moves along the FOV of the PA imaging system at step 106. In various aspects, the movement of the PA discontinuity may be monitored by measuring a change in position and a corresponding change in time of the PA discontinuity moving through the field of view. In one aspect, a minimum of two positions of the PA discontinuity within the field of view and two corresponding times may be measured at step 106. In other aspects, a plurality of positions of the PA discontinuity and a plurality of corresponding times may be measured at step 106.

Referring again to FIG. 11, the method 100 further includes calculating the blood flow speed using the positions and corresponding times of the PA discontinuity measured within the FOV by the PA imaging system at step 108. In various aspects, the blood flow speed is calculated by divided a change in position of the PA discontinuity by a corresponding change in time based on the at least two measurements of the PA discontinuity within the FOV obtained by the PA imaging device at step 106.

In one aspect, the change in the position of the PA discontinuity within the FOV may be obtained by subtracting a first position measured at a first time from a second position measured at a second time, and the corresponding change in time may be obtained by subtracting the first time from the second time. In this aspect, the blood flow speed is calculated by dividing the change in position by the change in time. In another aspect, a plurality of positions of the PA discontinuity and a plurality of corresponding times may be measured by the PA imaging system. In this aspect, the blood flow speed is calculated as the slope of a linear regression obtained for the plurality of positions as a function of the plurality of corresponding times.

In one aspect, the PA discontinuity within the blood flow is a blood surge produced applying a compression to a blood vessel to restrict blood flow through the vessel, and releasing the compression to induce a surge of densely-packed blood cells downstream of the compression release location. FIG. 12 is a flow chart illustrating the steps of a compression-based method 200 for measuring the velocity of blood flow in a blood vessel using a PA imaging system. Referring to FIG. 12, the field of view (FOV) of the PA imaging system may be aligned along the direction of blood flow within a segment of a blood vessel at step 202. A compression may be applied to the blood vessel as a position upstream of the FOV of the PA imaging system at step 204. Any known method or device may be used to apply the compression to the blood vessel including, but not limited to direct compression by a finger or other object, and inflation of a sphygmomanometer cuff to a pressure sufficient to compress the blood vessel. In various aspects, the compression is maintained on the blood vessel until almost no blood remains within the segment of the blood vessel within the FOV of the PA imaging system.

Referring again to FIG. 12, the compression on the blood vessel may be removed to cause a PA discontinuity in the form of a blood wash-in or blood surge to pass through the FOV of the PA imaging system at step 206. The movement of the PA discontinuity in the form of a blood surge may be monitored as described previously at step 208. The measured positions and corresponding sample times of the blood surge passing through the FOV of the PA imaging system may be used to calculate the blood flow speed at step 210, using methods similar to those described previously.

By way of non-limiting example, the blood flow upstream of the FOV may be stopped by cuffing the blood vessel with a sphygmomanometer. A high pressure of about 220 mg Hg may be maintained in the cuff for a short time (e.g., about 10 seconds) until there is almost no blood left in the vessel in the FOV. Finally, the sphygmomanometer cuff is quickly released, and the blood flow speed is calculated by monitoring the blood wash-in process through the FOV.

In another aspect, an amount of a fluid with high PA contrast relative to the blood may be injected into the vessel to induce a PA discontinuity in the blood flow as the injected fluid moves downstream of the injection site. FIG. 13 is a flow chart summarizing the steps of a PA contrast fluid injection-based method 300 of measuring blood flow speed within a blood vessel using a PA imaging system. Referring to FIG. 13, the method 300 includes positioning a field of view (FOV) of the PA imaging system along a segment of the blood vessel at step 302. The method 300 further includes injecting a bolus of a fluid at an injection site upstream of the FOV of the PA imaging system at step 304. In various aspects, the injected fluid produces a PA signal with high contrast relative to the PA signal produced by the blood flow, enabling the detection of a first fluid-blood interface at an upstream end of the fluid bolus or a second fluid-blood interface at a downstream end of the fluid bolus. In these various aspects, the first and second fluid-blood interfaces are characterized by distinct changes in PA signal response within a relatively small spatial extent, providing labeled portions of the flow through the blood vessel that move along the vessel at a velocity matched to the blood flow velocity.

Referring again to FIG. 13, the movement of the first or second fluid-blood interfaces may be monitored as each interface moves through the FOV of the PA imaging device at step 306. As described previously, the monitoring at step 306 may include obtaining a minimum of two positions and corresponding times of the first or second fluid-blood interface in one aspect. In another aspect, a plurality of positions and corresponding times for the first or second fluid-blood interface moving through the FOV of the PA imaging system may be measured at step 306. Referring again to FIG. 13, the blood flow speed may be calculated at step 308 using the measurements of at least two positions and corresponding times obtained at step 306, and using methods similar to the computational methods described previously.

The fluid injected into the blood vessel at step 304 may be any suitable fluid with relatively low or high PA signal response compared to red blood cells or other objects within the blood flow including, but not limited to, saline solution. In non-limiting example, to increase the PA signal changes due to flowing RBCs, saline is injected into the blood stream. As a result, at the saline-blood interfaces, the PA signals have sharp changes—the blood's PA signal is strong while saline's signal is negligibly low. Thus, by monitoring the time course of the PA signals from the interface, the flow velocity in the blood stream can be quantified. In addition, because saline is widely used for intravenous infusion, no extra saline injection is needed to determine blood flow speed using the methods described herein in such patients.

Measuring blood flow speed in the optical diffusive regime in humans has been a long-standing challenge for photoacoustic tomography. A cuffing-based method to quantify blood flow speed in humans with a handheld photoacoustic probe is disclosed herein. By cuffing and releasing the blood vessel, the blood flow speed downstream can be measured. Taking advantage of a handheld PA imaging probe, the disclosed method can potentially be used to monitor blood flow speed in the clinic and at the bedside.

The saline-injection-based method to quantify blood flow velocity in vivo with acoustic-resolution photoacoustic tomography is also disclosed. By monitoring the saline-blood-interface propagating in the blood vessel, the flow velocity can be resolved. This method was demonstrated in phantom experiments, described herein below, where a root-mean-square error of prediction of 0.29 mm/s was achieved. By injecting saline into a mouse tail vein covered with 1 mm chicken tissue, the flow velocity in the tail vein was capable of being measured at depths, which is especially pertinent to monitoring blood flow velocity in patients undergoing intravenous infusion.

Using the PA contrast fluid injection-based method 300 described previously and illustrated in FIG. 13, the flow velocity was extracted in three steps from the PA signals of the saline-blood interface (SBI). First, the whole process of the interface propagation through the field of view (FOV) of the transducer array was monitored. At each time point, a 2D image of the blood vessel was acquired and then converted to a one dimensional (1D) amplitude image via the Hilbert transformation, followed by taking the absolute value and then taking the peak amplitude. By piecing together all the 1D images at consecutive time points, a final 2D amplitude image of the SBI was achieved, as shown in FIG. 6A. Note that the x-axis of the 2D amplitude image is the displacement along the blood vessel and the y-axis of the 2D amplitude image is time. Second, at each time point, the 1D PA amplitude of the phantom blood vessel was fitted by an error function to extract the location of the SBI, as indicated by the mean value of the error function in FIG. 6B. Last, by tracking the SBI along the phantom blood vessel, the blood stream flow velocity was calculated. As shown in FIG. 6C, although only two measurements of the SBI sufficed to calculate the blood flow velocity, multiple measurements could improve the accuracy by linear fitting.

Considering the difficulty that ultrasound methods encounter in measuring slow blood flow and the oxygen saturation of hemoglobin ($sO_2$), PA-based deep flow and $sO_2$ measurement may enable metabolic rate of oxygen quantification in humans in a variety of clinical settings, which may lead to significant applications such as noninvasive tumor screening and blood disorder diagnosis.

Accompanying with the blood pressure measurement, perform routine blood perfusion monitoring to diagnose disease in early stage, such as peripheral arterial occlusive disease (see FIG. 9) and diabetes (see FIG. 10A, FIG. 10B, and FIG. 10C). Non-limiting examples of suitable applications of the PA-based blood flow speed measurement methods disclosed herein include: predicting the chance of a burn healing; monitoring suspicious moles to prevent them developing into melanomas using blood flow speed as a diagnostic parameter; monitoring patients undergoing intravenous infusion; intraoperative assessment of tissue viability by direct measurements of perfusion (blood flow) and oxygenation using the PA-based methods described herein; monitor blood flows during tumor resections, organ transplants and/ or surgical reconstructions; postoperative monitoring of surgical patients to avoid thrombus-related complications including stroke, heart attack, or acute liver injury such as ischemic hepatitis (shock liver); and monitor blood flow in patients diagnosed with hypertension patient or arrhythmia.

By way of non-limiting example, the assessment of burn depth, and as such, the estimation of whether a burn wound is expected to heal on its own within 21 days, is one of the most important roles of the burn surgeon. Sufficient blood flow to the skin is essential for burn healing. Monitoring the blood flow may predict the chance of a burn healing; thus, can increase the accuracy on clinical decisions regarding burn surgery.

EXAMPLES

The following examples demonstrate various aspects of the disclosure.

Example 1

Figure 1A:
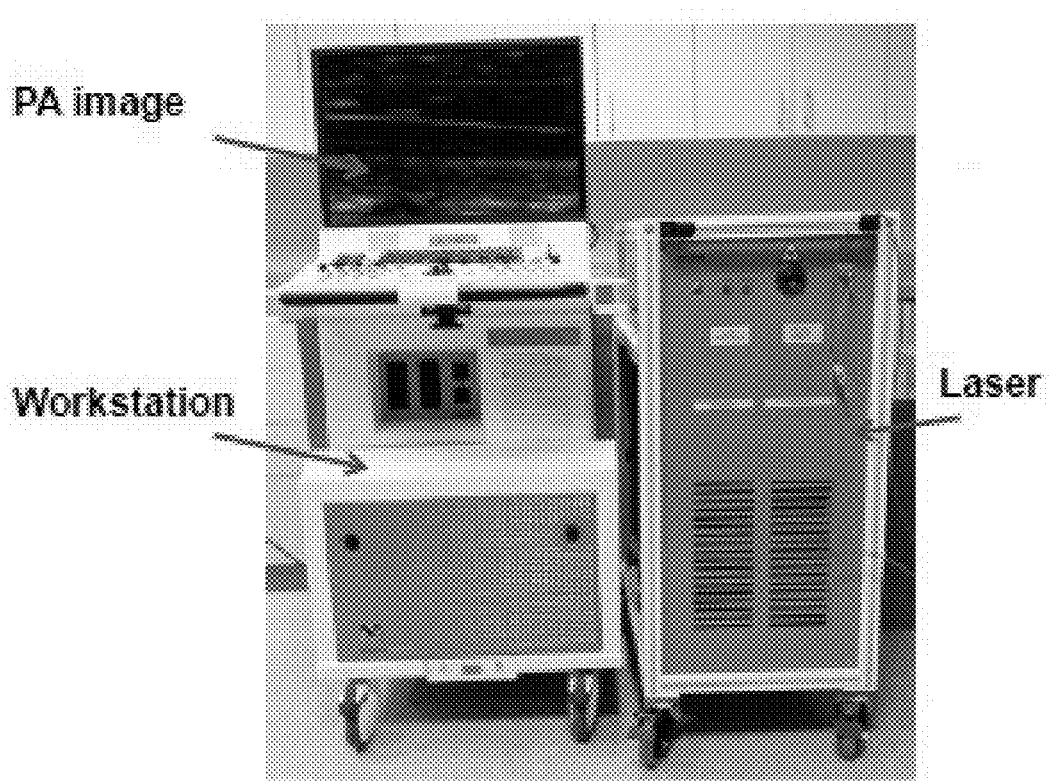
FIG. 1A is a photograph of a PAT system, including a workstation with a 64-channel data acquisition system, a data processing system, and an image display interface.
Figure 1B:
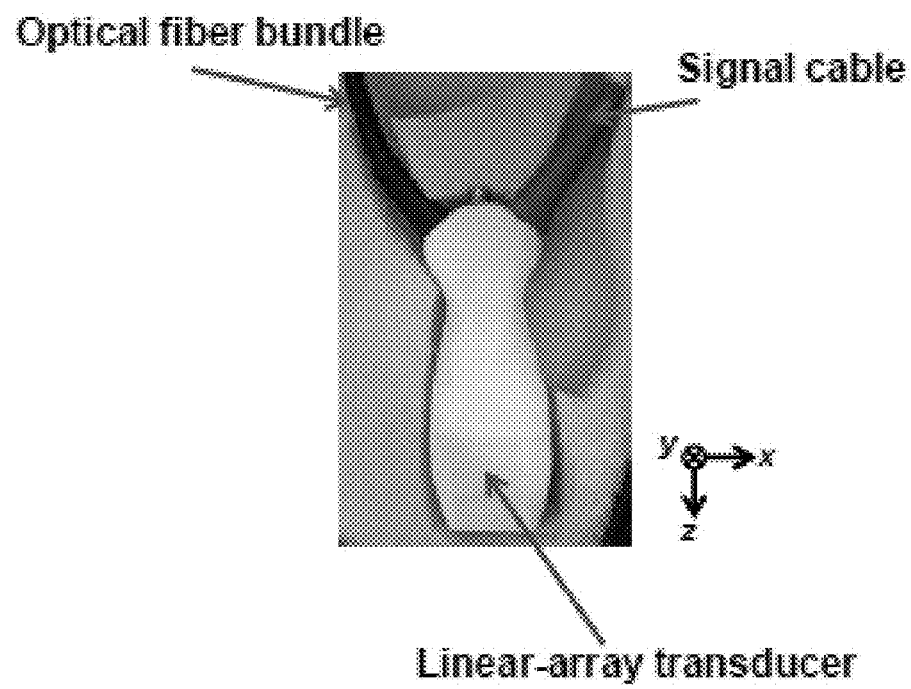
FIG. 1B is a photograph of a linear-array-transducer used with the PAT system depicted in FIG. 1A.

PAT Measurements of Flow Rate in Phantom Blood Vessel with Simulated Blood Wash-In To demonstrate the measurement of flow rate using the PAT imaging method described herein, the following experiment was conducted. A commercial PAT system (see FIG. 1A) with a linear-array ultrasound transducer (Vevo LAZR, VisualSonics, Toronto, ON, Canada), as shown in FIG. 1B, was used to perform PA imaging on a phantom blood vessel, described below. A schematic diagram of the PAT system is shown in FIG. 5A. The PAT system included an Nd:YAG laser combined with an optical parameter oscillator to provide tunable illumination wavelengths from 680 nm to 970 nm. The laser pulse produced by the PAT system had a pulse width around 10 ns and a pulse repetition rate of 20 Hz. The laser output was coupled to an optical fiber bundle that was divided into two rectangular fiber bundles (20 mm×1.25 mm) with an illumination angle of 60° directed toward the tissue surface of the phantom blood vessel. A 256-element linear-array-transducer, with a central frequency of around 21 MHz (one-way bandwidth, 78%) and a size of 20 mm×3 mm, detected ultrasonic signals in the PAT system. The transducer array and the fiber bundles were aligned coaxially and confocally to maximize the PAT system's sensitivity. A 4:1 electronic multiplexer was used to acquire ultrasonic signals from all the transducer elements over a 64-channel data acquisition system. Thus, using the 20 Hz laser, the two-dimensional frame rate was 5 Hz to obtain a full-width image. The frame rate could be increased up to 20 Hz with fewer receiving channels and thus a smaller field of view (FOV). In this experiment, a frame rate of 10 Hz was used with a FOV of about 12 mm×10 mm, along the axial and lateral directions of the array, respectively.

Figure 2A:
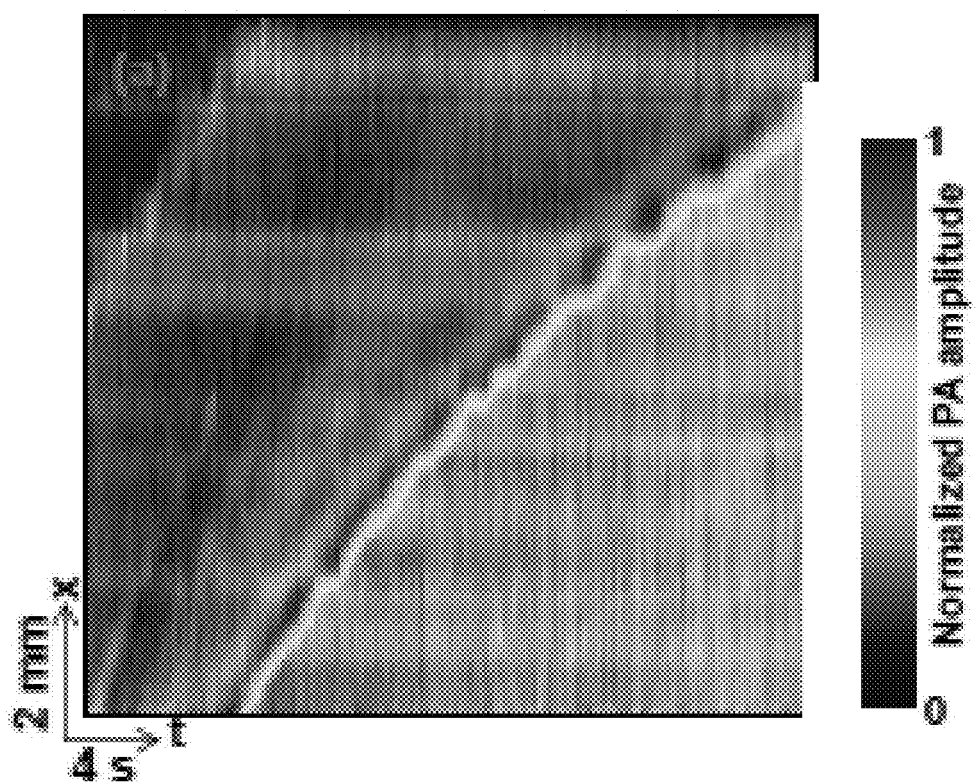
FIG. 2A is a graph summarizing PA signal amplitudes as a function of lateral position x and time t measured from a blood vessel phantom at a simulated flow speed of 0.14 mm/s.
Figure 2B:
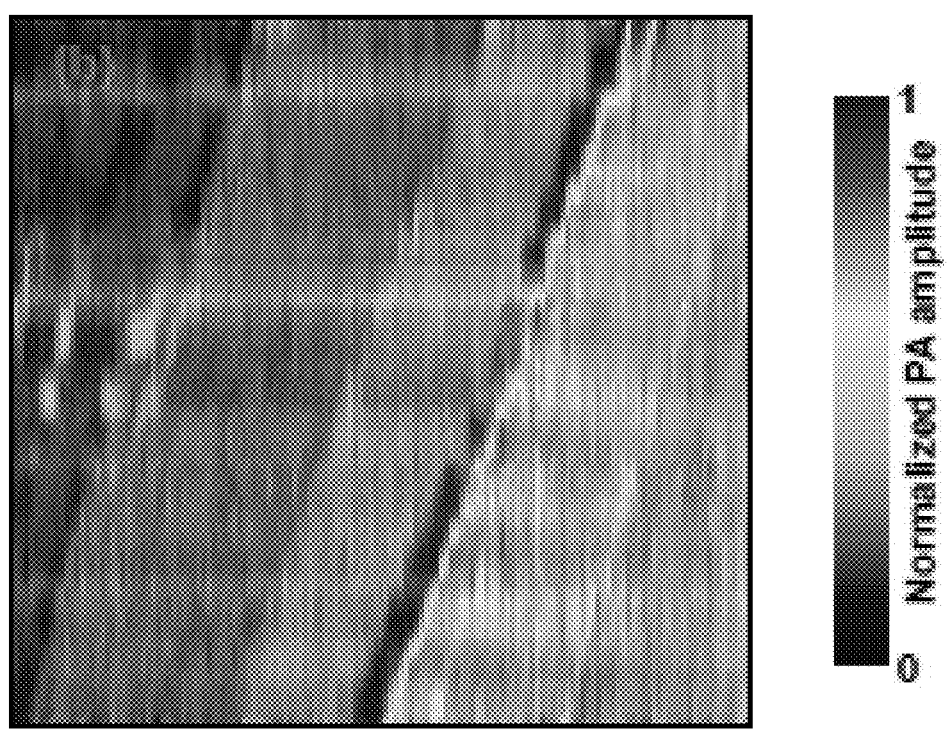
FIG. 2B is a graph summarizing PA signal amplitudes as a function of lateral position x and time t measured from a blood vessel phantom at a simulated flow speed of 1.1 mm/s.
Figure 2C:
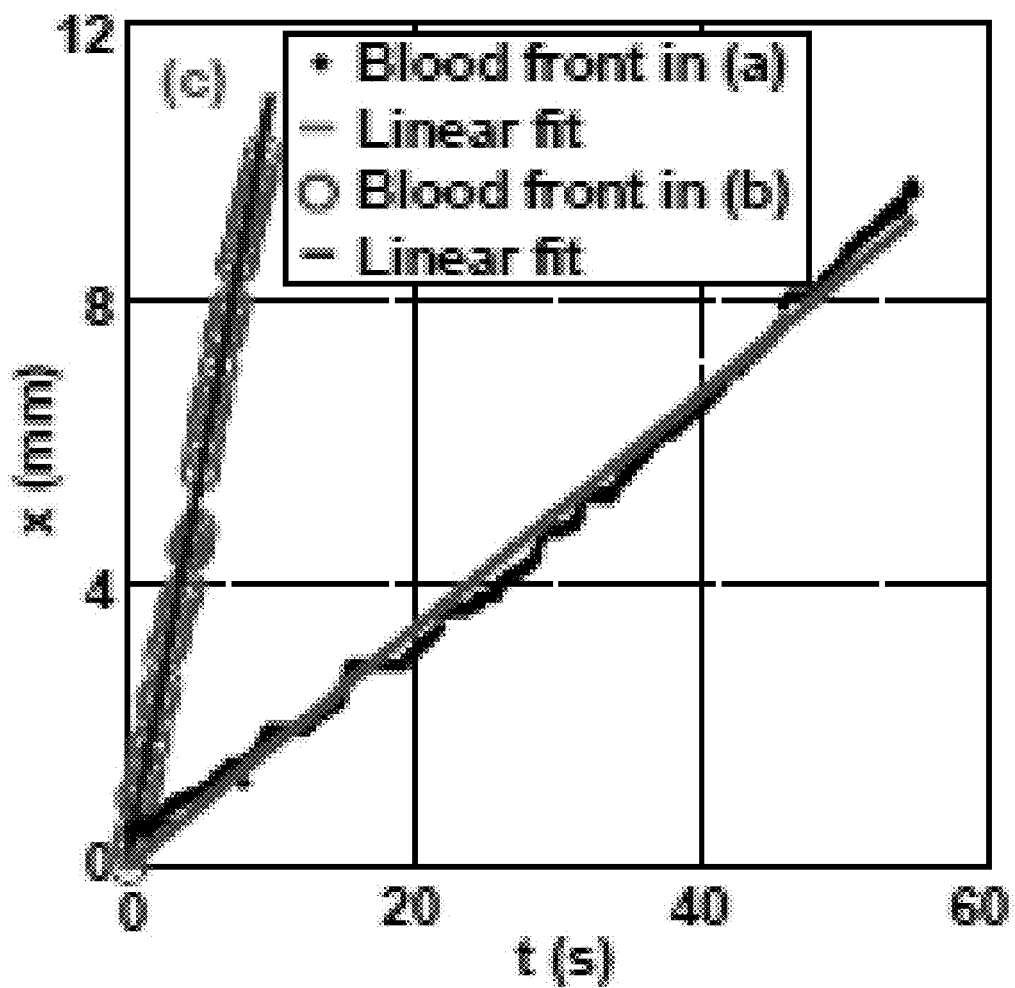
FIG. 2C is a graph summarizing the time course of the blood fronts illustrated in FIG. 2A and FIG. 2B, where the slope of each linear regression directly represents the flow speed.
Figure 2D:
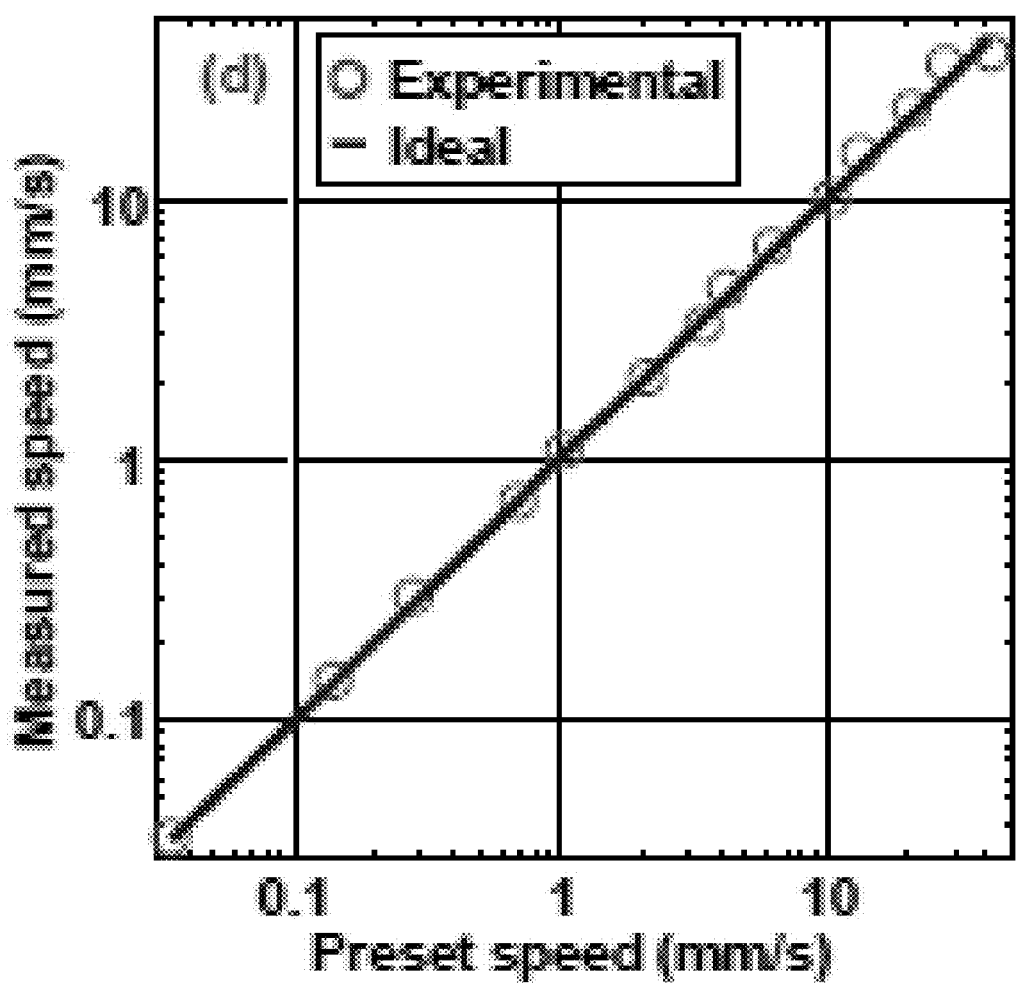
FIG. 2D is log-log graph summarizing the measured flow speeds as a function of the simulated flow speeds of the blood vessel phantom.

PAT imaging was performed on a blood vessel phantom to demonstrate the feasibility of the method disclosed herein for measuring blood flow speed in the diffusive regime. To mimic a deeply embedded blood vessel, silastic tubing with an inner diameter of 300 μm (11-189-15E, Fisher Scientific, Houston, Tex.) was overlaid by a piece of chicken breast tissue with a 2 mm thickness. Fresh bovine blood (910, QUAD FIVE INC., Ryegate, Mont.) was flowed inside the tubing at different preset flow speeds controlled by a syringe pump (BSP-99M, Braintree Scientific, Braintree, Mass.), as illustrated schematically in FIG. 5B. As shown in FIG. 2A and FIG. 2B, the blood wash-in process at different preset flow speeds (0.14 mm/s and 1.1 mm/s, respectively) was accurately imaged. In the images of FIG. 2A and FIG. 2B, each pixel column represents the one-dimensional PA amplitude image of the tubing in the FOV at a given time point. With increasing time, more blood flowed into the tubing in the imaging window. By quantifying the movement of the blood front formed by the initial volume of blood entering the phantom vessel at two or more different times, the flow speed was calculated, as shown in FIG. 2C. As shown in FIG. 2D, the measured flow speed agreed well with the preset values. The minimum measured flow speed was 0.035 mm/s, which is smaller than the typical blood flow speed in capillaries in humans and also slower than the lowest flow speed that Doppler US can measure, i.e., 1 mm/s.

Figure 2E:
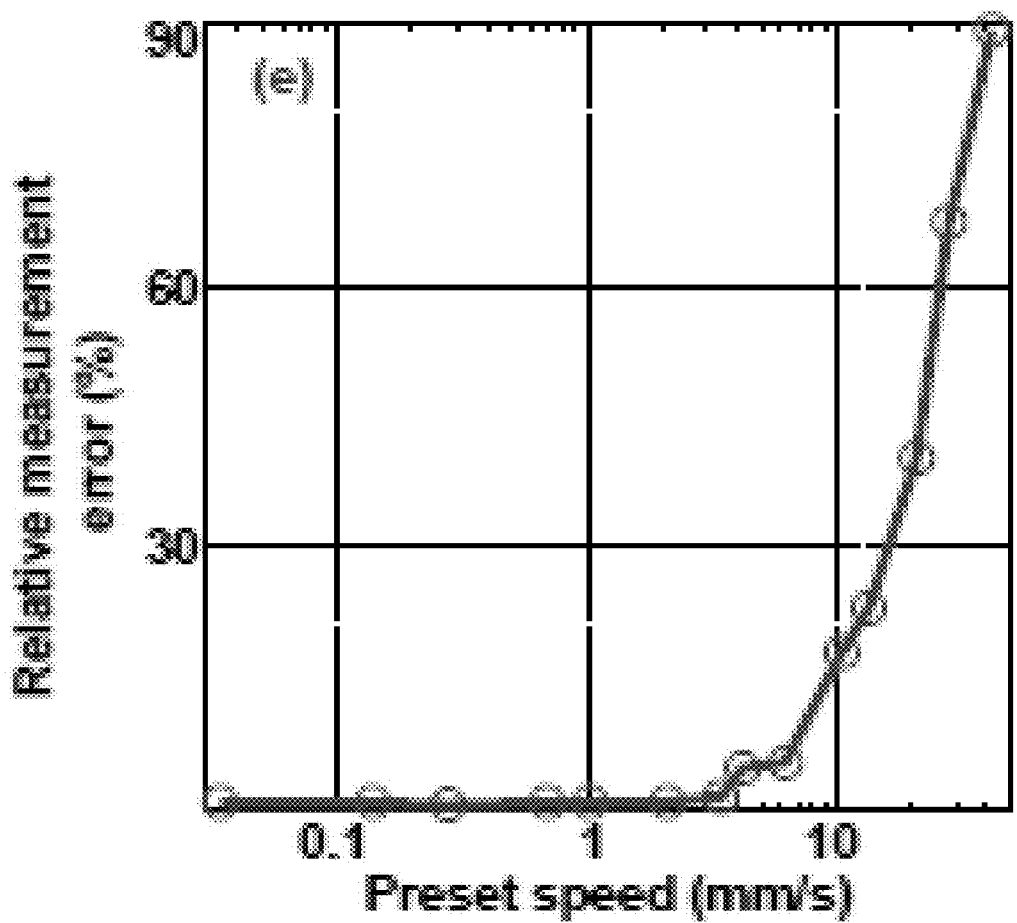
FIG. 2E is a semi-log graph summarizing the relative errors of the measured speeds with respect to the simulated flow speeds obtained from the graph shown in FIG. 2D.

The maximum measurable flow speed was also assessed as follows. To measure the moving speed of the blood front, the blood front in the phantom vessel was imaged at least twice. Thus, based on current frame rate (10 Hz) and FOV (10 mm along the tubing direction of the phantom blood vessel), the maximum measurable flow speed was theoretically predicted to be around 50 mm/s. However, as shown in FIG. 2E, as the preset flow speed increased, the measurement error increased as well, which was probably due to the decreased number of times that the blood front was imaged. In this experiment, the maximum measured flow speed was around 42 mm/s.

The results of this experiment demonstrated that blood flow speed was measurable within a range from about 0.35 mm/s to about 50 mm/s using the PAT imaging method described herein.

Example 2

Figure 3A:
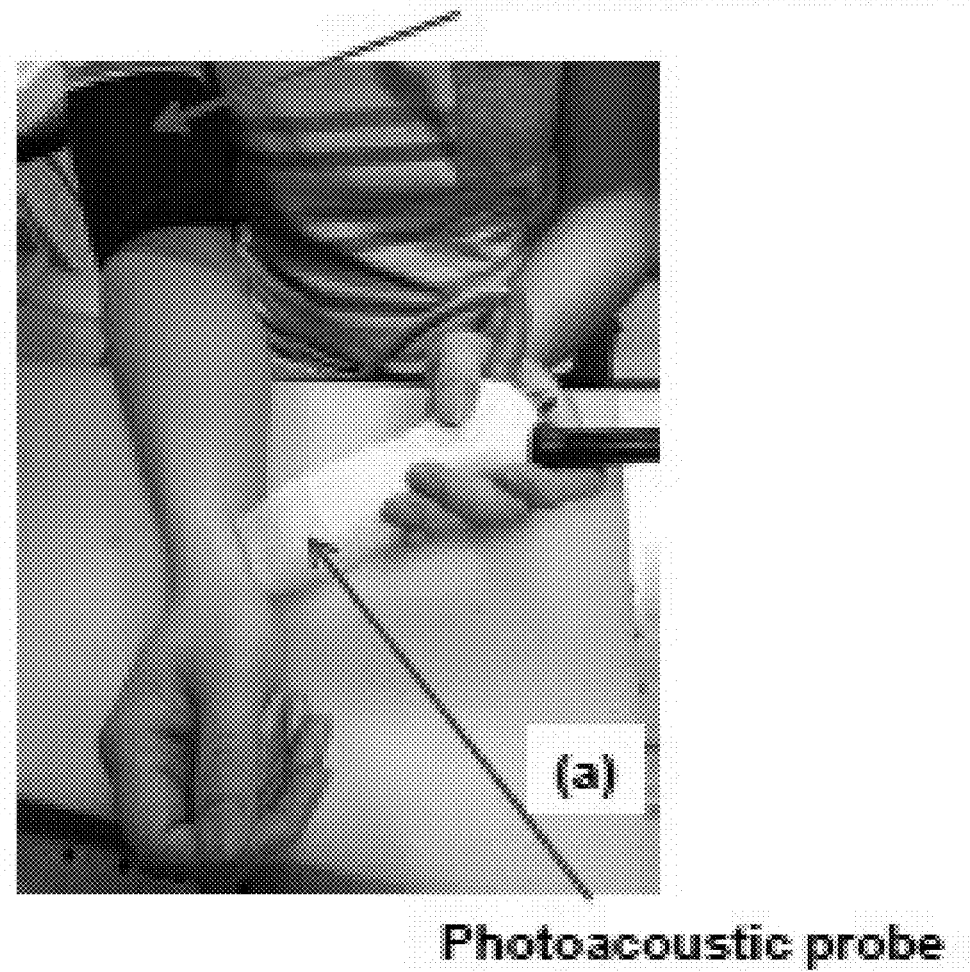
FIG. 3A is a photograph of a PAT-based blood flow measurement conducted at a forearm radial artery.
Figure 3B:
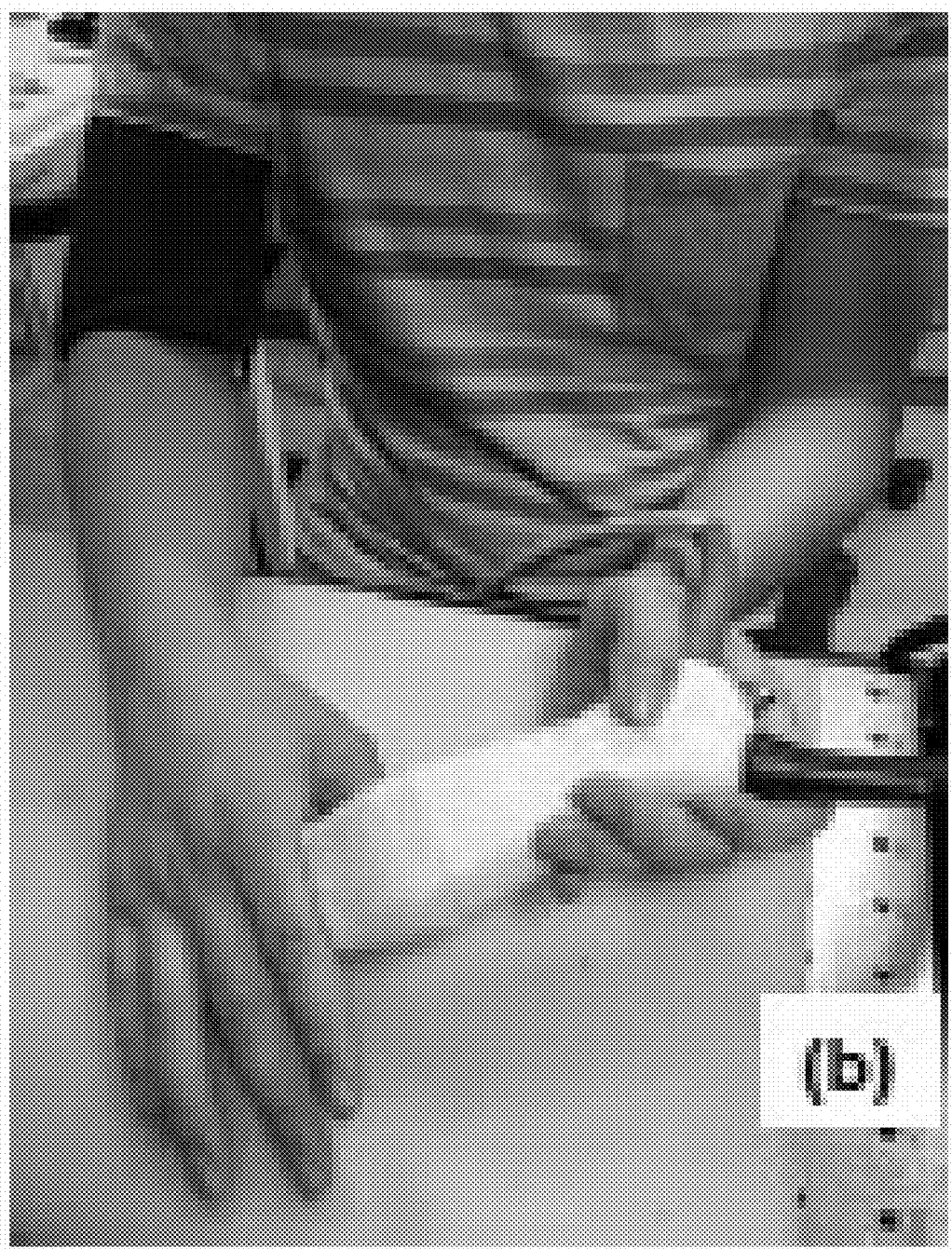
FIG. 3B is a photograph of a PAT-based blood flow measurement conducted at an index finger radial artery.
Figure 3C:
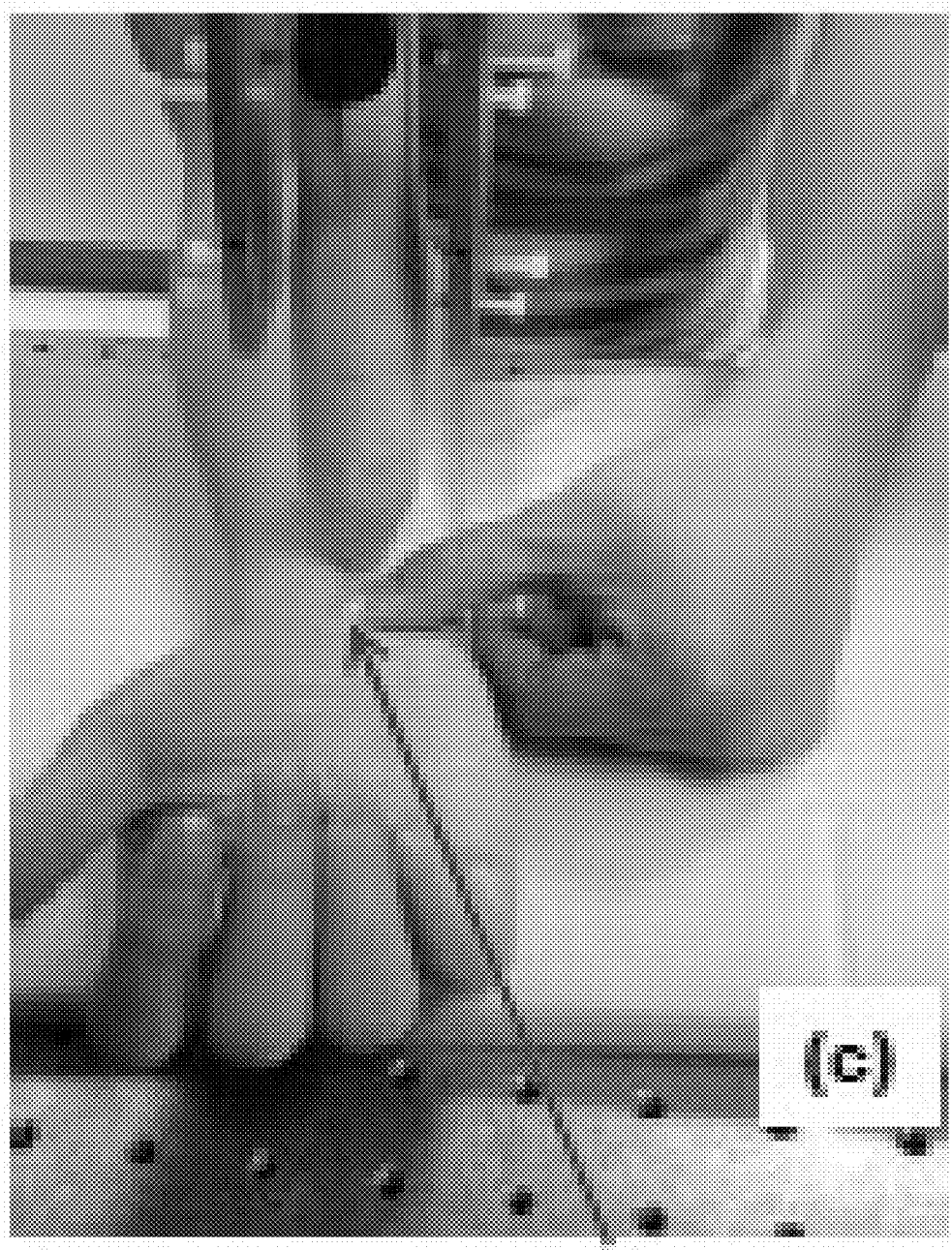
FIG. 3C is a photograph of a PAT-based blood flow measurement conducted at a forearm radial vein.

PAT Measurements of Flow Rate in Human Blood Vessel Using Blood Wash-In Following Release of Vessel Compression To demonstrate the measurement of flow rate using the PAT imaging method described herein in vivo on human subjects, the following experiment was conducted. As shown in FIGS. 3A, 3B, and 3C, PAT blood flow imaging was conducted at three different imaging sites on the human subjects: a radial artery in the right forearm (FIG. 3A), a radial artery in the index finger of the right hand (FIG. 3B), and a radial vein in the right forearm (FIG. 3C). As shown in FIGS. 3A and 3B, the upper arm was cuffed by the sphygmomanometer and then released while obtaining PAT images of the blood front to measure the blood flow speed in the radial arteries in the forearm and finger. To measure venous flow speed, instead of cuffing, the radial vein was directly compressed close to the wrist and a downstream location of the same vein was monitored, as shown in FIG. 3C. The PAT imaging system described in Example 1 was used to obtain images of the blood vessel at the three selected locations.

When the blood vessel was completely cuffed/compressed, there was almost no detectable blood in the downstream but blood accumulated under pressure upstream of the cuffing/compression spot. Thus, the initial post-release blood wash-in process was a surge, which diminished to normal flow with increased distance from the cuffing/compression spot. In the measurements of this experiment, surge effects were ameliorated by setting the downstream imaging locations at ~5 cm for the vein flow measurement and more than 30 cm for arterial measurements.

Figure 4A:
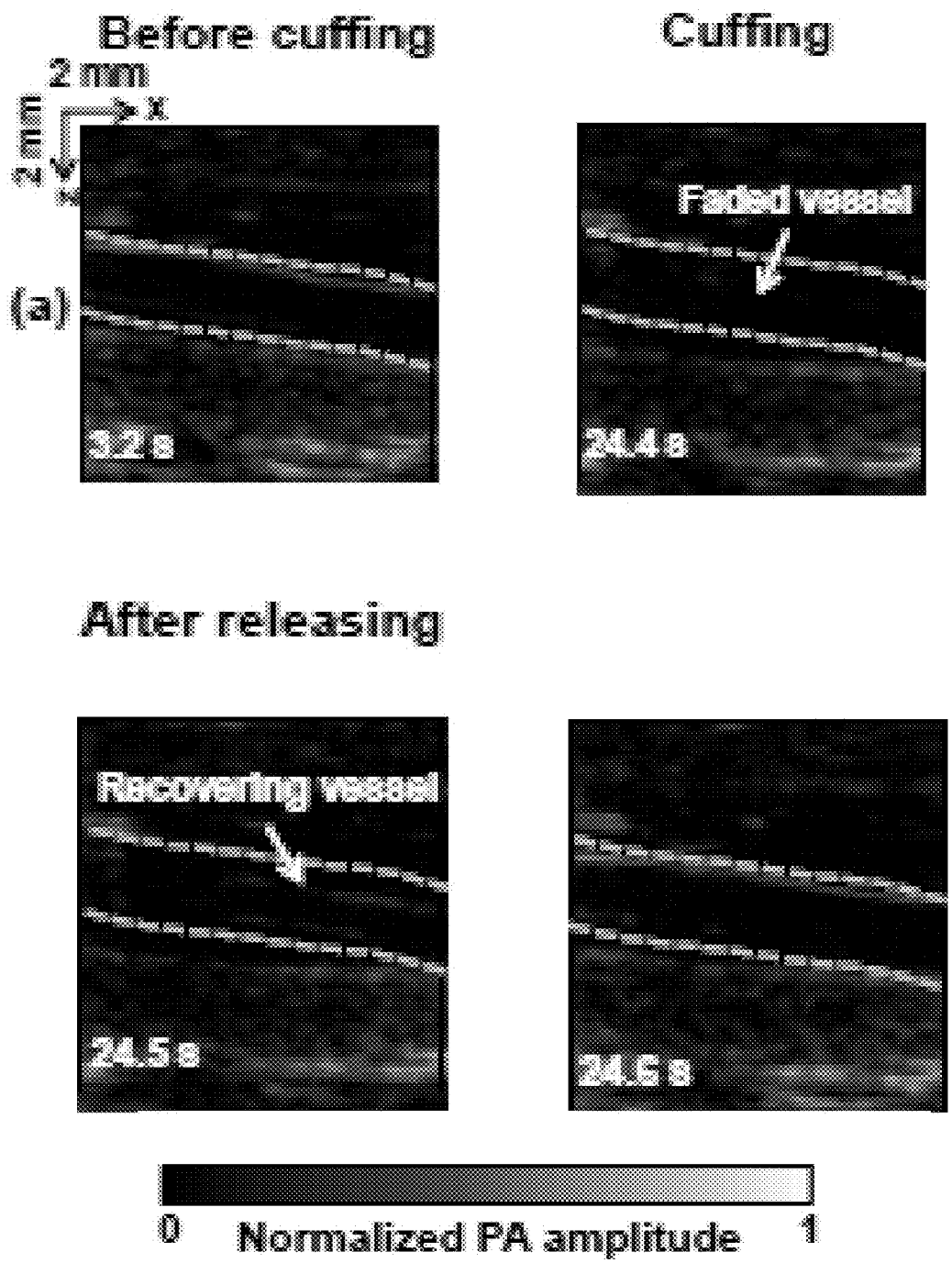
FIG. 4A is a series of PA images of a photograph of a forearm radial artery obtained before cuffing, during cuffing, and after releasing. The yellow dashed lines indicate the blood vessel regions.
Figure 4B:
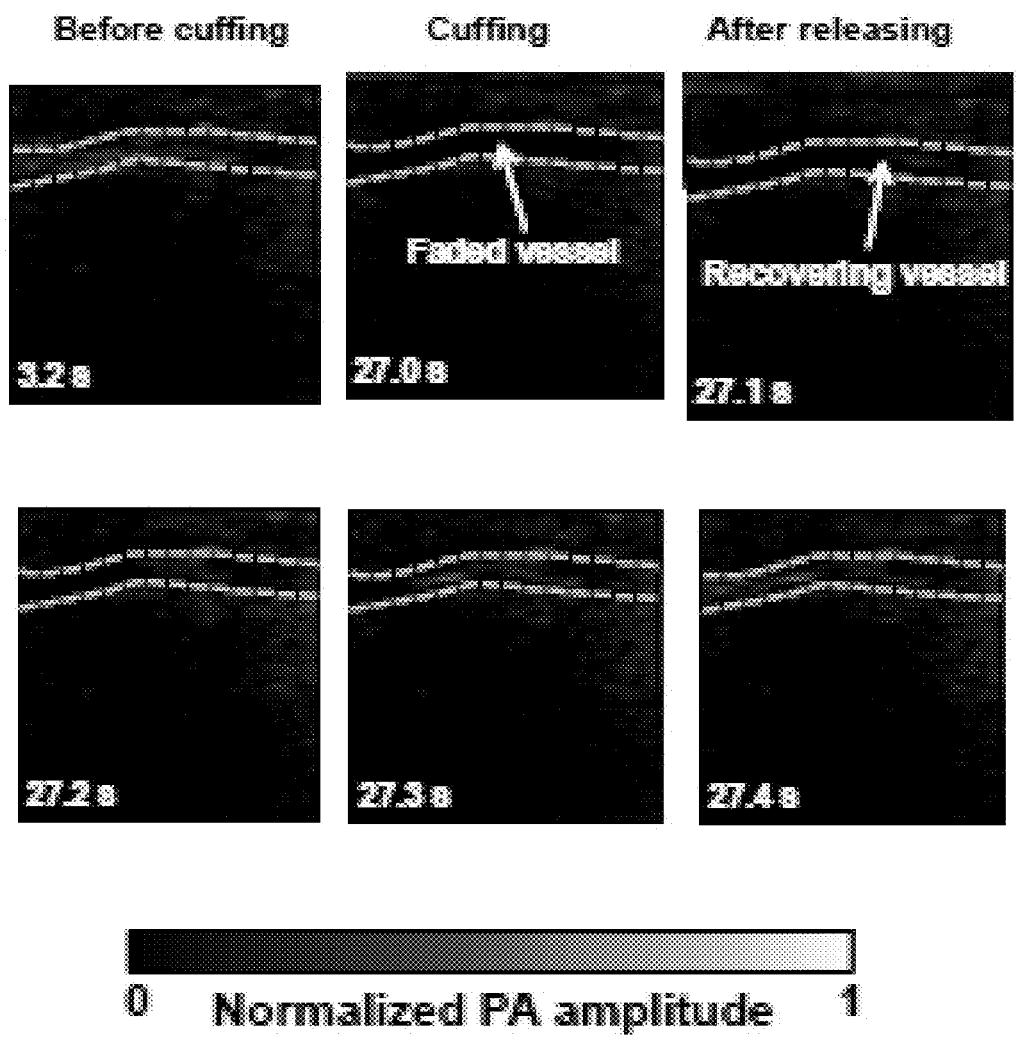
FIG. 4B is a series of PA images of a photograph of an index finger radial artery obtained before cuffing, during cuffing, and after releasing. The yellow dashed lines indicate the blood vessel regions.
Figure 4C:
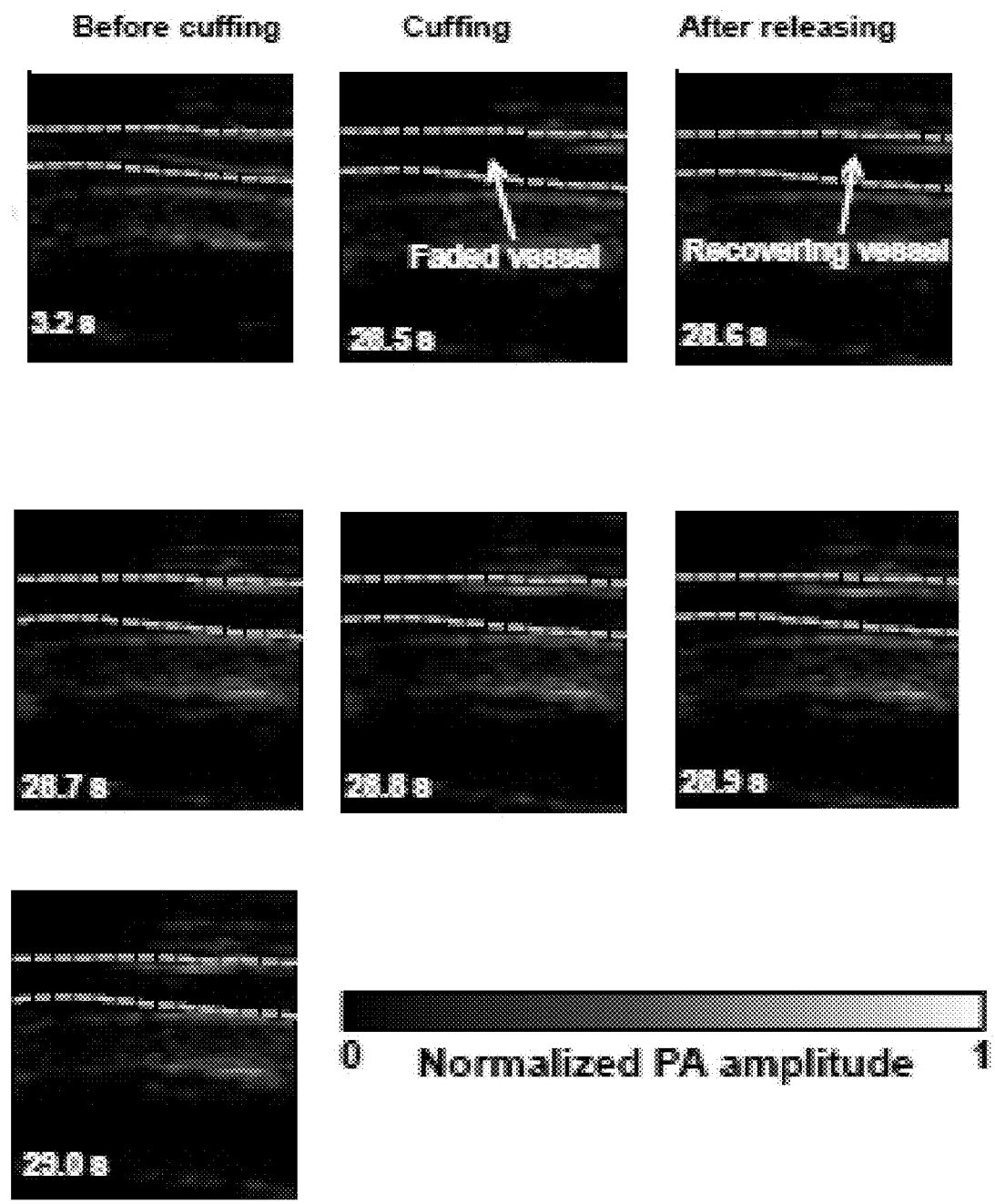
FIG. 4C is a series of PA images of a photograph of a forearm radial vein obtained before cuffing, during cuffing, and after releasing. The yellow dashed lines indicate the blood vessel regions.

As shown in FIGS. 4A, 4B, and 4C, the cuffing and releasing processes for all tested locations were clearly imaged. Before cuffing the vessel, both the top and bottom walls of the vessel could be detected. After cuffing, the blood vessel almost completely disappeared in the PA images. Once the cuff was released, the blood vessel appeared again. The recovery speed depended on the blood flow speed. For the radial artery in the right forearm (FIG. 4A), the recovery process was the fastest, the recovery of the radial artery in the index finger (FIG. 4B) recovered at an intermediate rate, and the radial vein in the right forearm (FIG. 4C) had the slowest recovery.

Based on the same procedure as described in Example 1, the flow speeds in the blood vessels tested were calculated to be around 44 mm/s (forearm radial artery), 20 mm/s (index finger radial artery), and 10 mm/s (forearm radial vein). The PAT-measured blood flow speeds were consistent to the flow speeds measured using US Doppler methods, which were 50 mm/s, 18 mm/s, and 9.3 mm/s, respectively. These experimental results demonstrated that the cuffing-based PA method described herein can measure blood flow in humans in vivo in both big and small blood vessels.

Example 3

PAT Measurements of Flow Rate in Phantom Blood Vessel With Simulated Saline Injection To demonstrate the measurement of blood flow rate using the PAT imaging method with saline injection as described herein, the following experiment was conducted.

Phantom experiments were performed with simulated blood flow and saline injection. To simulate blood flow in biological tissue at depths of the optical diffusive regime, fresh chicken breast tissue with a thickness of ~2 mm was laid atop the phantom blood vessel illustrated schematically in FIG. 5B. During a simulated blood flow performed using methods similar to the method described in Example 1, a saline flow was introduced via the saline syringe illustrated schematically in FIG. 5B. After commencement of the saline solution, PAT imaging was performed downstream of the saline injection to obtain 1D images of the movement of the saline-blood-interface (SBI).

An acoustic resolution photoacoustic tomography (AR-PAT) system similar to the system used in Example 1 was used to image the phantom blood vessel in this experiment. As shown in FIG. 5A, the light source was a tunable optical parametric oscillator laser with a repetition rate of 20 Hz. For deep tissue imaging, 680 nm light was chosen for the experiments. The light was first coupled into an optical fiber bundle, which was divided into two rectangular strips (20 mm×1.25 mm) at the output end. The incident pulse fluence on the tissue surface was controlled to be around 10 mJ/cm$^2$, which was within the safety limit set by the American National Standards Institute (20 mJ/cm$^2$) at this wavelength. A linear-array transducer containing 256 elements (LZ250, Visualsonics Inc.) was used to detect the PA signals. Each laser pulse generated a two-dimensional (2D) PA image. With a central frequency around 21 MHz and a 78% one-way bandwidth, the transducer array had an axial resolution of 86 µm. With a size of 23 mm×3 mm and a cylindrical focus at 15 mm, the transducer array provided a lateral resolution of 119 µm and an elevational resolution of 1237 µm.

With a transducer FOV of about 10 mm along the lateral direction, the system illustrated in FIG. 5A had a frame rate of about 10 Hz. The memory included in the system illustrated in FIG. 5A enabled a maximum of 1000 continuous frames to be stored. Assuming that the lateral resolution (119 µm) of the transducer array represents the minimum displacement detectable by the system, the minimum measureable flow speed is about 119 μm/50 s=2.38 μm/s. Using similar assumptions, the maximum detectable flow speed is about 50 mm/s based on the system's frame rate and FOV along the lateral direction. For both estimates, it is assumed that the SBI is imaged twice in order to measure the flow speed, for both the minimum and maximum measureable flow estimations.

FIG. 5B shows a schematic of saline injection in the simulated phantom blood vessel. A silicone tube (300 μm inner diameter) filled with blood was used to mimic the blood vessel. The blood was pumped into the tube through a syringe, and the preset flow speed was controlled by a syringe pump. A second syringe was employed to perpendicularly inject saline solution into the tube. The distance (d) between the injection point and the center of the field of view was set at 15 cm to minimize disturbances to the blood flow due to the saline injection.

FIGS. 7A, 7B, and 7C show three representative 2D amplitude images of the SBI similar to the images of FIGS. 2A and 2B, measured after a saline injection into the phantom blood vessel with preset simulated blood flow velocities of 0.2, 1.3, and 4.5 mm/s, respectively. Because of the strong optical absorption difference between blood and saline, SBIs were imaged by PAT with high contrast, as shown in FIGS. 7A, 7B, and 7C.

The flow velocity was extracted in three steps from the PA signals of the saline-blood interface (SBI) summarized in FIGS. 7A, 7B, and 7C. First, the whole process of the propagation of the SBI through the field of view (FOV) of the transducer array was monitored. At each time point, a 2D image of the blood vessel was acquired and then converted to a one dimensional (1D) amplitude image via the Hilbert transformation, followed by taking the absolute value and then taking the peak amplitude. By piecing together all the 1D images at consecutive time points (represented as pixel columns), a final 2D amplitude image of the SBI was achieved, as shown in FIG. 6A. Note that the x-axis of the image shown in FIG. 6A is the displacement along the blood vessel and the y-axis is time. Second, at each time point, the 1D PA amplitude of the phantom blood vessel was fitted by an error function to extract the location of the SBI, as indicated by the mean value of the representative error function in FIG. 6B. Last, by tracking the movement of the SBI over time along the phantom blood vessel, the blood flow velocity was calculated. As shown in FIG. 6C, although only two measurements of the SBI sufficed to calculate the blood flow velocity, multiple measurements improved the accuracy of the calculated blood flow velocity by linear fitting of multiple measurements.

Thus, by linear fittings of the SBI spatial-temporal locations using the data summarized in FIGS. 7A, 7B, and 7C as described above, the PAT-measured blood flow velocities obtained in this manner agreed well with the preset simulated blood flow rate values, as shown in FIG. 7D. The root-mean-square error of prediction (RMSEP) was calculated to be 0.29 mm/s, indicating that the PAT blood flow measurement method is capable of measuring blood flow in deep vessels with high accuracy.

The results of this experiment demonstrated the capability of measuring blood flow speed in deep vessels using PAT imaging of SBI in a simulated blood vessel over a range of blood flow speeds.

Example 4

PAT Measurements of Flow Rate in Mouse Tail Vein With Saline Injection

To demonstrate the use of PAT imaging of the movement of saline-blood interfaces (SBIs) in an animal subject in vivo, the following experiment was conducted. Blood flow velocity was measured in a mouse tail vein in vivo using methods similar to those described in Example 3 to demonstrate the detection ability of the saline-injection-based method. To simulate a deep vessel, a slice of chicken breast tissue (~1 mm) was put atop the tail vein to increase the measurement depth of a PAT system similar to the PAT system described in Example 3. During this experiment, an infrared lamp kept the mouse warm, and a breathing anesthesia system (E-Z Anesthesia, Euthanex) kept the mouse motionless. Saline was injected into the tail vein of the mouse with using a custom catheter to induce the SBI that was monitored by the PAT system to obtain the measurements to be analyzed for blood flow measurement using the method described in Example 3. The distance between the injection site and the imaging window of the PAT system was ~3 cm.

As shown in FIG. 8A, before saline injection, the whole tail vein in the field of view (FOV) of the linear transducer array of the PAT system could be clearly observed. However, when the saline flushed in, there were almost no signals from the blood vessel anymore because of the low absorption of saline, as shown in FIG. 8B. As the termination of the saline injection, the SBI's spatial-temporal location was clearly imaged by PAT, as shown in FIG. 8C. Based on the same procedure as in the phantom experiment described in Example 3, the blood flow velocity in the mouse tail vein was quantified to be around 4.5 mm/s.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A method of measuring a velocity of a blood flow in a blood vessel using a photoacoustic imaging system, the method comprising:
    positioning a 2D field of view of the photoacoustic imaging system along a segment of the blood vessel;
    introducing a photoacoustic discontinuity into the blood flow at a position upstream of the 2D field of view;
    obtaining, using the photoacoustic imaging system, at least two images of the 2D field of view and corresponding image acquisition times after introduction of the photoacoustic discontinuity;
    transforming each image to a 1D amplitude image associated with each corresponding image acquisition time, the 1D amplitude image comprising a plurality of PA amplitudes and corresponding positions along the segment of the blood vessel;
    transforming each 1D amplitude image to a position of the photoacoustic discontinuity associated with each image acquisition time; and
    calculating the velocity of the blood flow by dividing a difference between any two positions of the photoacoustic discontinuities by a difference between associated image acquisition times.

2. The method of claim 1, wherein the photoacoustic discontinuity is selected from: a blood surge and a bolus of a contrasting fluid.

3. The method of claim 2, wherein:
the photoacoustic discontinuity is the blood surge comprising a dense bolus of blood cells bounded by a blood surge interface at a downstream end of the bolus; and
the photoacoustic discontinuity is introduced by:
applying a compression to the blood vessel upstream of the field of view for a time sufficient to deplete the segment of the blood vessel of blood cells downstream of the compression and to form a blood surge upstream of the compression; and
releasing the compression from the blood vessel causing the blood surge to flow within the blood vessel to the field of view of the photoacoustic imaging system.

4. The method of claim 3, wherein the compression is applied by one of:
directly pressing on the blood vessel; and
inflating a sphygmomanometer cuff to a pressure sufficient to compress the blood vessel.

5. The method of claim 2, wherein:
the photoacoustic discontinuity is the bolus of the contrasting fluid bounded by a first fluid-blood-interface at an upstream end and by a second fluid-blood interface at a downstream end; and
the photoacoustic discontinuity is introduced by injecting the bolus of the contrasting fluid into the blood vessel upstream of the field of view causing the bolus to flow within the blood vessel to the field of view of the photoacoustic imaging system.

6. The method of claim 2, wherein the bolus of the contrasting fluid is injected using an injection device selected from: a syringe and a catheter.

7. The method of claim 2, wherein the contrasting fluid comprises a saline solution.

8. The method of claim 7, wherein the contrasting fluid further comprises at least one additional photoacoustic contrast agent that produces a contrasting PA signal compared to a blood PA signal produced by the blood flow.

9. The method of claim 1, wherein transforming each image to a 1D amplitude image comprises converting each image to a transformed image using a Hilbert transformation, obtaining absolute values of each pixel of the transformed image, and selecting a peak amplitude among a plurality of amplitudes corresponding to each position along the segment of the blood vessel.

10. The method of claim 1, wherein transforming each 1D amplitude image to a position of the photoacoustic discontinuity comprises fitting an error function to each 1D amplitude image and selecting a position of the error function corresponding to an amplitude of 0.5 as the position of the photoacoustic discontinuity.

11. The method of claim 1, wherein the position at which the photoacoustic discontinuity is introduced and the field of view are separated by a distance sufficient to eliminate a transient change in the velocity of the blood flow associated with the introduction of the photoacoustic discontinuity.

12. A method of measuring a velocity of a blood flow in a blood vessel using a photoacoustic imaging system, the method comprising:
positioning a 2D field of view of the photoacoustic imaging system along a segment of the blood vessel;
applying a compression to the blood vessel upstream of the 2D field of view for a time sufficient to deplete the segment of the blood vessel of blood cells downstream of the compression and to form a blood surge upstream of the compression;
releasing the compression from the blood vessel causing the blood surge to flow within the blood vessel to the field of view of the photoacoustic imaging system, wherein the blood surge comprises a dense bolus of blood cells bounded by a blood surge interface at a downstream end of the bolus;
obtaining, using the photoacoustic imaging system, at least two images of the 2D field of view and corresponding image acquisition times after introduction of the blood surge;
transforming each image to a 1D amplitude image associated with each corresponding image acquisition time, the 1D amplitude image comprising a plurality of PA amplitudes and corresponding positions along the segment of the blood vessel;
transforming each 1D amplitude image to a position of photoacoustic discontinuity associated with each image acquisition time; and
calculating the velocity of the blood flow by dividing a difference between any two positions of the blood surges by a difference between associated image acquisition time.

13. The method of claim 12, wherein the compression is applied by one of:
directly pressing on the blood vessel; and
inflating a sphygmomanometer cuff to a pressure sufficient to compress the blood vessel.

14. The method of claim 12, wherein transforming each image to a 1D amplitude image comprises converting each image to a transformed image using a Hilbert transformation, obtaining absolute values of each pixel of the transformed image, and selecting a peak amplitude among a plurality of amplitudes corresponding to each position along the segment of the blood vessel.

15. The method of claim 12, wherein transforming each 1D amplitude image to a position of the photoacoustic discontinuity comprises fitting an error function to each 1D amplitude image and selecting a position of the error function corresponding to an amplitude of 0.5 as the position of the photoacoustic discontinuity.

16. The method of claim 12, wherein the position at which the blood surge is introduced and the field of view are separated by a distance sufficient to eliminate a transient change in the velocity of the blood flow associated with the introduction of the blood surge.

17. A system for measuring a velocity of a blood flow in a blood vessel, the system comprising:
a photoacoustic imaging system configured to obtain at least two images of a photoacoustic discontinuity flowing through a segment of a blood vessel within a 2D field of view and corresponding image acquisition times;
a photoacoustic discontinuity device configured to introduce the photoacoustic discontinuity into the segment of the blood vessel at a position upstream of the 2D field of view; and
a photoacoustic discontinuity detection device configured to transform each image to a 1D amplitude image associated with each corresponding image acquisition time, the 1D amplitude image comprising a plurality of PA amplitudes and corresponding positions along the segment of the blood vessel, and to transform each 1D amplitude image to a position of the photoacoustic discontinuity associated with each image acquisition time; and calculating the velocity of the blood flow is calculated by dividing a difference between any two positions of the photoacoustic discontinuity by a difference between associated image acquisition times.

18. The system of claim 17, wherein the photoacoustic discontinuity device is selected from:

a compression device configured to reversibly occlude the blood vessel by applying compression to the blood vessel, wherein the photoacoustic discontinuity is introduced into the blood flow in the form of a blood surge interface released when the compression to the blood vessel is removed; and an injection device configured to inject a bolus of a contrasting fluid into the blood vessel, wherein the photoacoustic discontinuity is introduced into the blood flow in the form of a fluid-blood interface released at injection.

19. The system of claim 18, wherein the compression device is selected from a sphygmomanometer cuff and a tourniquet.

20. The system of claim 18, wherein the injection device is selected from a syringe and a catheter.

* * * * *